(12) United States Patent
Jung et al.

(10) Patent No.: US 12,339,256 B2
(45) Date of Patent: Jun. 24, 2025

(54) GLASS STRENGTH EVALUATION APPARATUS AND METHOD

(71) Applicant: Samsung Display Co., LTD., Yongin-si (KR)

(72) Inventors: So Mi Jung, Busan (KR); Seung Kim, Seongnam-si (KR); Seung Ho Kim, Anyang-si (KR); Hyun Chul Bae, Yongin-si (KR); Hui Yeon Shon, Seongnam-si (KR); Gyu In Shim, Hwaseong-si (KR); Hoi Kwan Lee, Suwon-si (KR)

(73) Assignee: SAMSUNG DISPLAY CO., LTD., Gyeonggi-Do (KR)

( * ) Notice: Subject to any disclaimer, the term of this patent is extended or adjusted under 35 U.S.C. 154(b) by 402 days.

(21) Appl. No.: 17/870,834

(22) Filed: Jul. 22, 2022

(65) Prior Publication Data

US 2023/0184647 A1 Jun. 15, 2023

(30) Foreign Application Priority Data

Dec. 9, 2021 (KR) .......................... 10-2021-0175265

(51) Int. Cl.
*G01N 3/08* (2006.01)

(52) U.S. Cl.
CPC ....... *G01N 3/08* (2013.01); *G01N 2203/0017* (2013.01); *G01N 2203/0019* (2013.01); *G01N 2203/0032* (2013.01)

(58) Field of Classification Search
None
See application file for complete search history.

(56) References Cited

U.S. PATENT DOCUMENTS

| | | | |
|---|---|---|---|
| 11,454,579 B2 * | 9/2022 | Takeda | .................. G01N 21/59 |
| 2012/0135852 A1 | 5/2012 | Ellison et al. | |
| 2016/0215381 A1 | 7/2016 | Levine et al. | |
| 2016/0369387 A1 | 12/2016 | Ciraldo et al. | |
| 2017/0305786 A1 | 10/2017 | Roussev et al. | |

(Continued)

FOREIGN PATENT DOCUMENTS

| | | |
|---|---|---|
| DE | 102014108057 | 12/2015 |
| JP | 2000028482 | 1/2000 |

(Continued)

*Primary Examiner* — Peter J Macchiarolo
*Assistant Examiner* — Jermaine L Jenkins
(74) *Attorney, Agent, or Firm* — CANTOR COLBURN LLP

(57) ABSTRACT

A glass strength evaluation apparatus includes a support unit, a plate disposed on the support unit and including a surface on which a glass article, which is a target to be tested, is disposed, a fixing jig disposed on the plate and a power unit lifting up or down the fixing jig in a vertical direction toward the surface of the plate. The fixing jig includes a body portion, which extends in the vertical direction and lower fixing bolts. A press-fitting member insertion opening is recessed from a bottom of the body portion to extend in an upward direction, lower fixing bolt insertion holes penetrate the body portion, from one side of the body portion, in a first horizontal direction intersecting the vertical direction, to be extended to the press-fitting insertion opening, and lower fixing bolts are coupled into the lower fixing bolt insertion holes.

20 Claims, 21 Drawing Sheets

(56) References Cited

U.S. PATENT DOCUMENTS

| | | | |
|---|---|---|---|
| 2017/0341973 | A1 | 11/2017 | Gross et al. |
| 2018/0155235 | A1 | 6/2018 | Beall et al. |
| 2020/0165162 | A1 | 5/2020 | Bellman et al. |
| 2021/0208039 | A1 | 7/2021 | Farooqi et al. |

FOREIGN PATENT DOCUMENTS

| | | |
|---|---|---|
| JP | 2006071415 | 3/2006 |
| JP | 2015206663 | 6/2020 |
| JP | 2020094867 | 6/2020 |
| KR | 20110073798 | 6/2011 |
| KR | 101323998 | 10/2013 |
| KR | 1020150087648 | 7/2015 |
| KR | 1020150129732 | 11/2015 |
| KR | 1020150140570 | 12/2015 |
| KR | 1020170130498 | 11/2017 |
| KR | 1020180007044 | 1/2018 |
| KR | 1020180057814 | 5/2018 |
| KR | 101902597 | 9/2018 |
| KR | 20180137066 | 12/2018 |
| KR | 1020180136490 | 12/2018 |
| KR | 1020190012143 | 2/2019 |
| KR | 102005785 | 7/2019 |
| KR | 1020190099233 | 8/2019 |
| KR | 1020200038883 | 4/2020 |
| WO | WO-2022116025 A1 * | 6/2022 |

* cited by examiner

GLASS STRENGTH EVALUATION APPARATUS AND METHOD

This application claims priority to Korean Patent Application No. 10-2021-0175265, filed on Dec. 9, 2021, and all the benefits accruing therefrom under 35 U.S.C. § 119, the content of which in its entirety is herein incorporated by reference.

BACKGROUND

1. Field

Embodiments of the disclosure relate to a glass strength evaluation apparatus and method.

2. Description of the Related Art

Glass articles are widely used in electronic devices with display devices, building materials, and the like. Glass articles may be applied to substrates of flat panel display devices such as liquid crystal displays ("LCDs"), organic light-emitting diode ("OLED") displays, or electrophoretic displays ("EPDs") or to windows protecting the substrates.

As portable electronic devices such as smartphones and tablet personal computers (PCs) increase, the glass articles applied to such devices are often exposed to external shock. Thus, the strength of glass articles is measured before or after assembling the glass articles with other parts or elements to check the durability of the glass articles. Therefore, a method is desired to improve the precision of the measurement of glass strength.

SUMMARY

Features of the disclosure provide a glass strength evaluation apparatus.

Features of the disclosure also provide a glass strength evaluation method.

However, features of the disclosure are not restricted to those set forth herein. The above and other features of the disclosure will become more apparent to one of ordinary skill in the art to which the disclosure pertains by referencing the detailed description of the disclosure given below.

In an embodiment of the disclosure, a glass strength evaluation apparatus includes a support unit, a plate disposed on the support unit and including a surface on which a glass article, which is a target to be tested is disposed, a fixing jig disposed on the plate and a power unit which lifts up or down the fixing jig in a vertical direction toward the first surface of the plate. The fixing jig includes a body portion, which extends in the vertical direction, and through which lower fixing bolt insertion holes penetrate in a first horizontal direction intersecting the vertical direction, and lower fixing bolts which are coupled into the lower fixing bolt insertion holes. A press-fitting member insertion opening is recessed from a bottom of the body portion to extend in an upward direction, and is extended to the lower fixing bolt insertion holes.

In an embodiment, the lower fixing bolt insertion holes may include a first lower fixing bolt insertion hole and a second lower fixing bolt insertion hole, which is disposed below the first lower fixing bolt insertion hole.

In an embodiment, the first and second lower fixing bolt insertion holes may be arranged along the vertical direction.

In an embodiment, the lower fixing bolt insertion holes may include screw grooves on inner sidewalls thereof, and the lower fixing bolts may include screw threads corresponding to the screw grooves.

In an embodiment, the glass strength evaluation apparatus may further include a coupling unit connected to a lower part of the power unit, the fixing jig may further include a coupling head, which is connected to an upper part of the body portion and has a smaller outer diameter than an outer diameter of the body portion, and the coupling unit may further include a head receiving portion, which receives the coupling head.

In an embodiment, the coupling head may include a head fixing pin insertion hole, which penetrates the coupling head in a second horizontal direction intersecting the vertical direction, from a first side of the coupling head to a second side of the coupling head, and the coupling unit may include a first upper fixing pin insertion hole, which penetrates the coupling unit in the second horizontal direction from a first side of the coupling unit corresponding to the first side of the coupling head toward the head receiving portion, and a second upper fixing pin insertion hole, which penetrates the coupling unit in the second horizontal direction from a second side of the coupling unit corresponding to the second side of the coupling head toward the head receiving portion.

In an embodiment, the glass strength evaluation apparatus may further include an upper fixing pin extending across the first upper fixing pin insertion hole, the head fixing pin insertion hole, and the second upper fixing pin insertion hole.

In an embodiment, the glass strength evaluation apparatus may further include a press-fitting member inserted in the press-fitting member insertion opening.

In an embodiment, the press-fitting member may extend in the vertical direction, a first end of the press-fitting member may be exposed at the bottom of the body portion, and a second end of the press-fitting member may be inserted in the press-fitting member insertion opening.

In an embodiment, the press-fitting member may include an indenter, which is disposed at the first end and has a ball shape.

In an embodiment, the indenter may have a diameter of about 0.3 millimeter (mm) to about 1 mm.

In an embodiment, the indenter may include a chromium alloy (100Cr6).

In an embodiment, the glass strength evaluation apparatus may further include a load setting circuit setting a load for the glass article and a descending speed of the power unit and a controller controlling an operation of the power unit.

In an embodiment, the glass strength evaluation apparatus may further include a sensor unit which is disposed on the first surface of the plate and senses a load applied to the glass article and a breakage of the glass article.

In an embodiment, the glass article may have a thickness of about 50 micrometers (μm) to about 100 μm.

According to yet another feature of the disclosure, a glass strength evaluation method includes placing a glass article including first and second surfaces on a first surface of a plate such that an entirety of the second surface of the glass article contacts the first surface of the plate, lifting down a press-fitting member, which extends in a vertical direction and includes an indenter having a ball shape at one end of the press-fitting member, in the vertical direction such that the indenter contacts the first surface of the glass article and increasing a load applied to the first surface of the glass article through the indenter by gradually lifting down the press-fitting member in the vertical direction and determining whether the glass article is broken.

In an embodiment, the indenter may have a diameter of about 0.3 mm to about 1 mm.

In an embodiment, the indenter may include a chromium alloy (100Cr6).

In another embodiment of the disclosure, a glass strength evaluation method includes coupling a first press-fitting member, which extends in a vertical direction and includes a first indenter having a ball shape at one end of the first press-fitting member, to a fixing jig, placing the fixing jig on a plate such that the first press-fitting member faces a top of the plate, placing a first glass article included in the glass article and including first and second surfaces on a first surface of the plate such that an entirety of the second surface of the first glass article contacts the first surface of the plate, lifting down the fixing jig such that the first indenter contacts the first surface of the first glass article and increasing a load applied to the first surface of the first glass article through the first indenter by gradually lifting down the fixing jig in the vertical direction and determining whether the first glass article is broken.

In an embodiment, the glass strength evaluation method may further include after the determining whether the first glass article is broken, retrieving the first glass article and separating the first press-fitting member from the fixing jig, coupling a second press-fitting member, which extends in the vertical direction and may include a second indenter having a ball shape at one end of the second press-fitting member, to the fixing jig, placing the fixing jig on the plate such that the second press-fitting member faces the top of the plate, placing a second glass article included in the glass article and including first and second surfaces on the first surface of the plate such that an entirety of the second surface of the second glass article contacts the first surface of the plate, lifting down the fixing jig such that the second indenter contacts the first surface of the second glass article, and increasing a load applied to the first surface of the second glass article through the second indenter by gradually lifting down the fixing jig in the vertical direction and determining whether the second glass article is broken.

According to the aforementioned and other embodiments of the disclosure, a glass strength evaluation apparatus and method capable of improving the precision of evaluation and estimating test results from other glass strength evaluation methods with a similar mechanism may be provided.

It should be noted that the effects of the disclosure are not limited to those described above, and other effects of the disclosure will be apparent from the following description.

BRIEF DESCRIPTION OF THE DRAWINGS

The above and other features and features of the disclosure will become more apparent by describing in detail embodiments thereof with reference to the attached drawings, in which.

DETAILED DESCRIPTION

Figure 1:
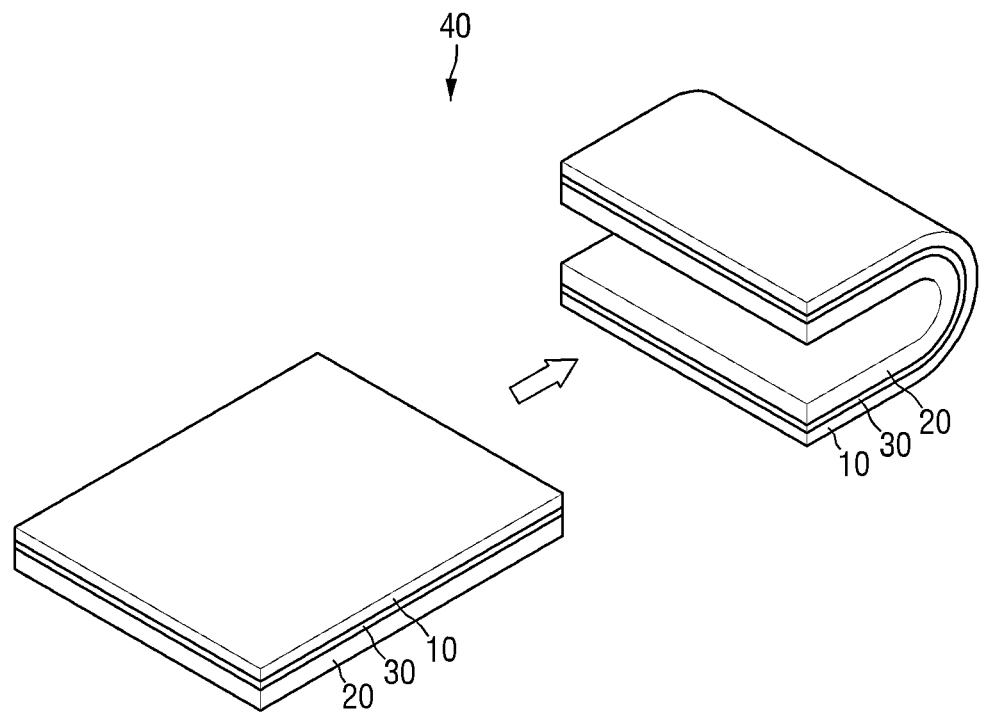
FIG. 1 is a perspective view illustrating an example in which a glass article is applied to a cover window for a display device.

Embodiments of the disclosure will now be described more fully hereinafter with reference to the accompanying drawings, in which preferred embodiments of the disclosure are shown. This disclosure may, however, be embodied in different forms and should not be construed as limited to the embodiments set forth herein. Rather, these embodiments are provided so that this disclosure will be thorough and complete, and will filly convey the scope of the disclosure to those skilled in the art.

It will also be understood that when a layer is referred to as being "on" another layer or substrate, it can be directly on the other layer or substrate, or intervening layers may also be. The same reference numbers indicate the same components throughout the specification.

It will be understood that, although the terms "first," "second," etc. may be used herein to describe various elements, these elements should not be limited by these terms. These terms are only used to distinguish one element from another element. For instance, a first element discussed below could be termed a second element without departing from the teachings of the disclosure. Similarly, the second element could also be termed the first element.

The terminology used herein is for the purpose of describing particular embodiments only and is not intended to be limiting. As used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the Figures. It will be understood that relative terms are intended to encompass different orientations of the device in addition to the orientation depicted in the Figures. In an embodiment, when the device in one of the figures is turned over, elements described as being on the "lower" side of other elements would then be oriented on "upper" sides of the other elements. The exemplary term "lower," can therefore, encompasses both an orientation of "lower" and "upper," depending on the particular orientation of the figure. Similarly, when the device in one of the figures is turned over, elements described as "below" or "beneath" other elements would then be oriented "above" the other elements. The exemplary terms "below" or "beneath" can, therefore, encompass both an orientation of above and below.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). The term "about" can mean within one or more standard deviations, or within ±30%, 20%, 10%, 5% of the stated value, for example.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the disclosure, and will not be interpreted in an idealized or overly formal sense unless expressly so defined herein.

Hereinafter, embodiments of the disclosure will be described in detail with reference to the accompanying drawings.

FIG. 1 is a perspective view illustrating an example in which a glass article is applied to a cover window for a display device.

Referring to FIG. 1, glass may be used not only in a tablet personal computer ("PC"), a notebook PC, a smartphone, an electronic book (e-book) reader, a television ("TV"), or a PC monitor, but also in a cover window for an electronic device (such as a refrigerator, a washing machine, or the like) with a display device, a substrate for a display panel, a substrate for a touch panel, or an optical member such as a light guide plate. Glass may also be used as cover glass for an automobile dashboard, cover glass for a solar cell, a material for the interior of a building, or a window of a building or a house.

FIG. 1 illustrates an example in which a glass article 10 is applied as a cover window for a display device 40. Referring to FIG. 1, the display device 40 may include a display panel 20, the glass article 10, which is disposed on the display panel 20, an optically clear bonding layer 30, which is disposed between the display panel 20 and the glass article 10 and bonds the display panel 20 and the glass article 10 together.

The display panel 20 may include a plurality of pixels and may display an image with the use of light emitted from the pixels. The display device 40 may further include a touch member (not illustrated). The touch member may be internalized in the display panel 20. In an embodiment, as the touch member is formed or disposed directly on a display member of the display panel 20, the display panel 20 may perform a touch function, for example. In an alternative embodiment, the touch member may be manufactured separately from the display panel 20 and may then be attached to the top surface of the display panel 20 by an optically clear bonding layer.

The glass article 10 is disposed on the display panel 20. The glass article 10 protects the display panel 20, from above the display panel 20. The glass article 10, which is used as a cover window for the display device (e.g., foldable display device) 40, may be ultrathin tempered glass. In an embodiment, the ultra-thin tempered glass may have a thickness of about 300 micrometers (μm) or less or about 100 μm or less.

The glass article 10 will hereinafter be described.

Figure 2:
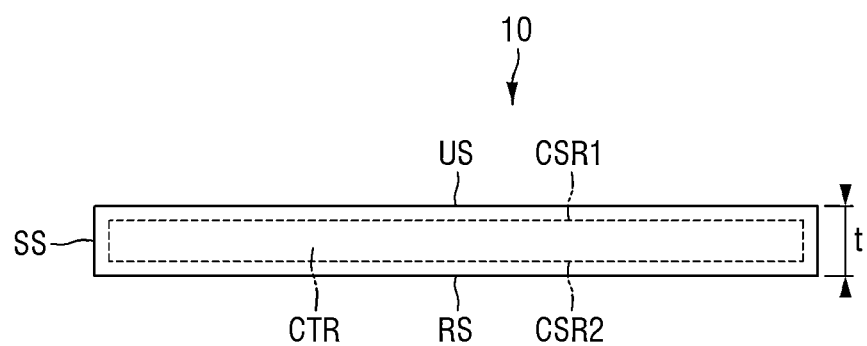
FIG. 2 is a cross-sectional view of the glass article of FIG. 1.

FIG. 2 is a cross-sectional view of the glass article of FIG. 1.

Referring to FIG. 2, the glass article 10 may have multiple surfaces (US, RS, and SS), i.e., a first surface US, a second surface RS, and side surfaces SS. The first and second surfaces US and RS of the glass article 10, which is in the shape of a flat plate, may be main surfaces (e.g., top and bottom surfaces) of the glass article 10 that have a large area, and the side surfaces SS may be outer surfaces that extend from (or connect) the first and second surfaces US and RS. The first and second surfaces US and RS may be opposite to each other in a direction of a thickness T. In a case where the glass article 10 serves the function of the window of a display device, i.e., the function of transmitting light therethrough, light may enter through one of the first and second surfaces US and RS and may be output through the other surface.

The thickness t of the glass article 10 is defined as the distance between the first and second surfaces US and RS. The glass article 10 may be ultrathin tempered glass. The thickness t of the glass article 10 may be between 10 μm and 300 μm. In an embodiment, the thickness t of the glass article 10 may be about 100 μm or less, for example. In another embodiment, the thickness t of the glass article 10 may be about 70 μm or less. In another embodiment, the thickness t of the glass article 10 may be about 50 μm or less. In another embodiment, the thickness t of the glass article 10 may be about 30 μm or less. However, the disclosure is not limited to these embodiments. The thickness t of the glass article 10 may be uniform, but may differ from one area to another aera.

The glass article 10 includes compressive regions (CSR1 and CSR2) and a tensile region CTR. The compressive regions (CSR1 and CSR2) are regions to which compressive stress is applied, and the tensile region CTR is a region to which tensile stress is applied. The compressive regions (CSR1 and CSR2) are disposed adjacent to the surfaces (US, RS, and SS) of the glass article 10 and the tensile region CTR is disposed on the inside (or the middle) of the glass article 10. The compressive regions (CSR1 and CSR2) may be disposed adjacent not only to the first and second surfaces US and RS, but also to the side surfaces SS. The depth (or the compression depth) of the compressive regions (CSR1 and CSR2), which extend in a depth direction from each of the surface US, RS, and SS, may be substantially uniform, but the disclosure is not limited thereto. The tensile region CTR may be surrounded by the compressive regions (CSR1 and CSR2).

Figure 3:
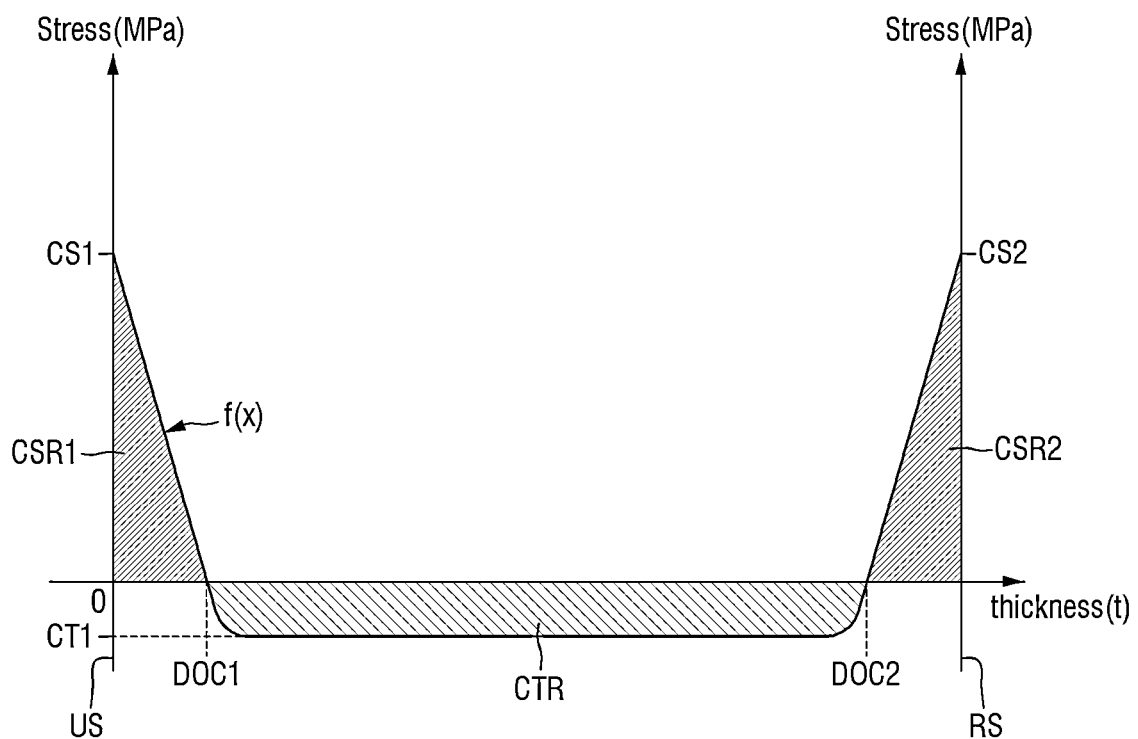
FIG. 3 is a graph showing the stress profile of the glass article of FIG. 1.

FIG. 3 is a graph showing the stress profile f(x) of the glass article of FIG. 1.

Referring to FIG. 3, the X axis represents the direction of the thickness t of the glass article 10, compressive stress is represented as a positive value, and tensile stress is reed as a negative value. Here, the magnitude of compressive/tensile stress may refer to the absolute value of the compressive/tensile stress.

Referring to FIGS. 2 and 3, the glass article 10 includes the first compressive region CSR1, which extends to a first depth (or a first compression depth DOC1) from the first surface US, and a second compressive region CSR2, which extends to a second depth (or a second compression depth DOC2) from the second surface RS2.

The tensile region CTR is disposed between the first and second compression depths DOC1 and DOC2. Although not specifically illustrated, other compressive and tensile regions may be further between the side surfaces SS of the glass article 10.

The first and second compressive regions CSR1 and CSR2 resist external impact to mitigate the formation of cracks in the glass article 10 or the breakage of the glass article 10. It may be understood that the strength of the glass article 10 becomes greater as the greater maximum compressive stresses CS1 and CS2 of the first and second compressed regions CSR1 and CSR2 become greater. As external impact is usually transmitted through the surfaces (US, RS, and SS) of the glass article 10, it is advantageous, in terms of durability, for the glass article 10 to have the maximum compressive stresses CS1 and CS2 at the surfaces (US, RS, and SS) of the glass article 10.

The first and second compression depths DOC1 and DOC2 suppress the propagation of any cracks or grooves on the first and second surfaces US and RS into the tensile region CTR in the glass article 10. As the first and second compression depths DOC1 and DOC2 become greater, the glass article 10 can better prevent the propagation of cracks.

FIG. 3 shows a stress profile across the first and second surfaces US and RS along a thickness direction. As similar ion exchanges to those on the first and second surfaces US and RS may occur on the side surfaces SS, a similar stress profile to that of the first compressive region CSR1 may be obtained from the side surfaces SS.

Referring to FIG. 3, the sum of the areas of the first and second compressive regions CSR1 and CSR2 may be the same as the area of the tensile region CTR.

The tensile stress of the tensile region CTR may be balanced with the compressive stress of the first and second compressive regions CSR1 and CSR2. That is, the total compressive stress (or compressive energy) in the glass article 10 may be the same as the total tensile stress (or tensile energy) in the glass article 10. Specifically, the sum of the compressive stress (i.e., first compressive energy) of the first compressive region CSR1 and the compressive stress (i.e., second compressive energy) of the second compressive region CSR2 may be the same as the tensile stress (or tensile energy) of the tensile region CTR. As the tensile stress in the glass article 10 becomes greater, the glass article 10 is more likely to shatter from the inside, releasing fragments violently. In a case where the glass article 10 has a thickness t of about 50 μm or less, the thickness of the tensile region CTR may not be sufficiently secured, and as a result, the magnitude of the tensile stress of the tensile region CTR may be large. Thus, the glass article 10 may be broken, releasing fragments violently. In an embodiment, when the glass article 10 is broken during annealing during tempering or during annealing after tempering, fine glass particles may be generated as fragments, for example.

In an embodiment, the glass article 10 may have a maximum tensile stress CT1 of about 100 megapascals (MPa) or greater, about 150 MPa or greater, or about 200 MPa or greater, but the disclosure is not limited thereto.

The maximum tensile stress CT1 of the glass article 10 may be disposed in a middle portion of the glass article 10 in the direction of the thickness t. In an embodiment, the maximum tensile stress CT1 of the glass article 10 may be disposed at a depth of about 0.4t to about 0.6t, about 0.45t to about 0.55t, or about 0.5t, for example.

The first and second compression depths DOC1 and DOC2 suppress the propagation of any cracks or grooves on the first and second surfaces US and RS into the tensile region CTR in the glass article 10. As the first and second compression depths DOC1 and DOC2 become greater, the propagation of cracks or grooves may be better suppressed. Locations corresponding to the first and second compression depths DOC1 and DOC2 may be the boundaries between the tensile region CTR and the first and second compressive regions CSR1 and CSR2, and the stress at the locations corresponding to the first and second compression depths DOC1 and DOC2 may be zero.

The glass article 10 may have the above-described stress profile through the tempering of mother glass. The stress profile of the glass article 10 may vary depending on a set of conditions for the tempering of mother glass. A stress profile determines the strength of the glass article 10, but the relationship between the pattern of the stress profile of the glass article 10 and the actual strength of the glass article 10 is desired to be experimentally confirmed to identify the properties of the glass article 10.

When designing process conditions for forming a stress profile, the temperature and the duration of an ion exchange process and whether the ion exchange process involves thermal treatment may be considered, and the stress profile and the strength of the glass article 10 may vary depending on the designed process conditions.

However, even when processes are performed in accordance with the designed process conditions, an actual product obtained from the processes may have a different stress profile and strength from a designated stress profile and strength, depending on the composition and state of mother glass and a set of detailed parameters for each of the designed process conditions.

The strength of the glass article 10 may be evaluated by, e.g., a ring-on-ring evaluation method.

Figure 4:
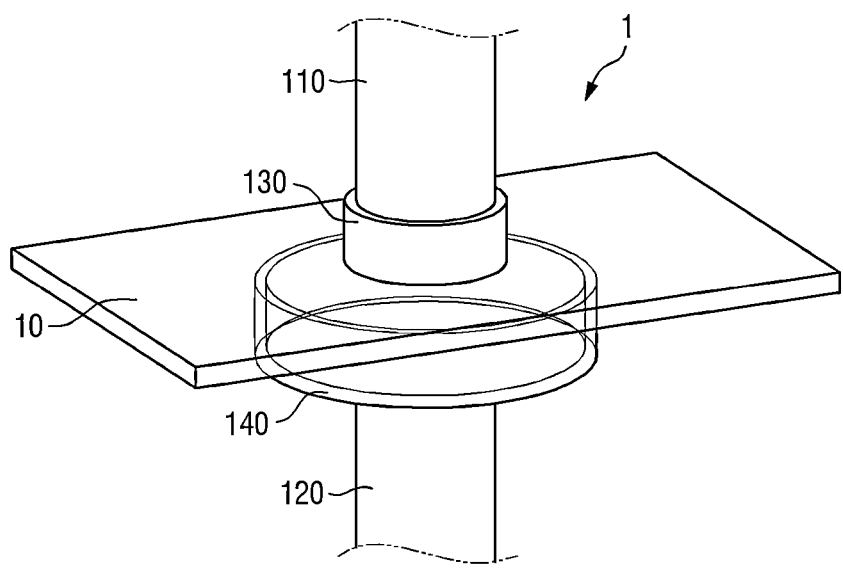
FIG. 4 is a perspective view of a ring-on-ring evaluation apparatus.
Figure 5:
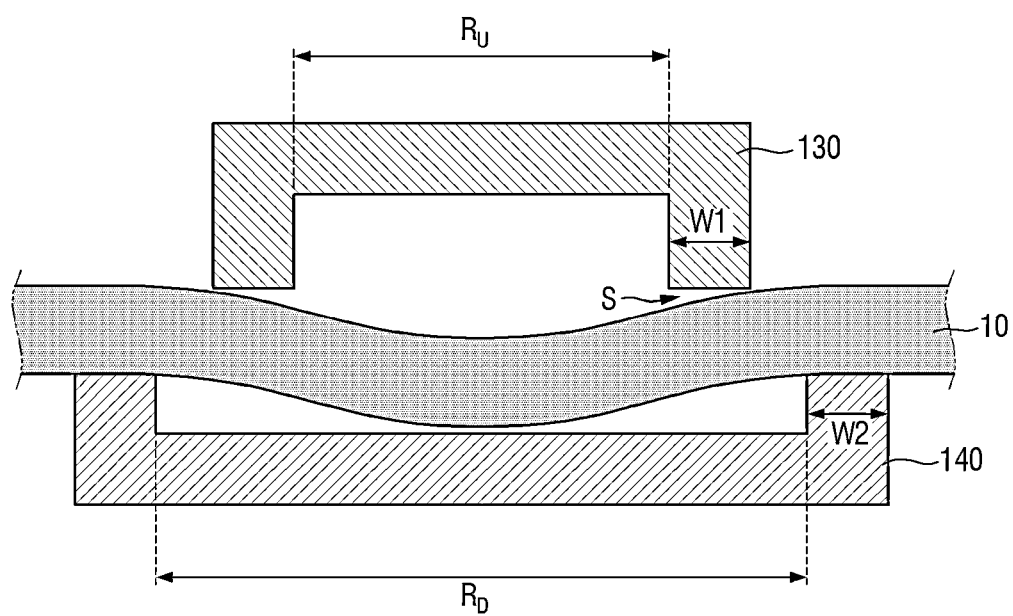
FIG. 5 is a cross-sectional view illustrating how slip concern area is generated during the measurement of a glass article by a ring-on-ring evaluation apparatus.

FIG. 4 is a perspective view of a ring-on-ring evaluation apparatus. FIG. 5 is a cross-sectional view illustrating how slip concern area is generated during the measurement of a glass article by a ring-on-ring evaluation apparatus.

Referring to FIGS. 4 and 5, a ring-on-ring evaluation apparatus 1 includes upper and lower rings 130 and 140. The lower ring 140 may have a larger inner diameter than an inner diameter of the upper ring 130. In an embodiment, the upper ring 130 may have an inner diameter $R_U$ of about 6.3 millimeter (mm), and the lower ring 140 may have an inner diameter $R_D$ of about 12.6 mm.

The upper and lower rings 130 and 140 may be disposed to be a predetermined distance apart from each other in a vertical direction. The upper and lower rings 130 and 140 may be disposed to have the same center.

To evaluate the strength of the glass article 10, the glass article 10 is inserted between the upper and lower rings 130 and 140. The upper and lower rings 130 and 140 may be connected to upper and lower jigs 110 and 120, respectively, and as the upper ring 130 is pressed against the lower ring 140 by the upper jig 110, which applies a force in the vertical direction, the top surface of the glass article 10 may adjoin, and receive pressure from, the bottom surface of the upper ring 130, and the bottom surface of the glass article 10 may adjoin, and receive pressure from, the top surface of the lower ring 140. As the upper jig 110 applies further pressure, the breakage of the glass article 10 may begin, and the strength of the glass article 10 may be determined based on the level of pressure at the time of breakage of the glass article 10.

For the precision of the measurement of the strength of the glass article 10, pressure may be applied to the upper ring 130 and/or the lower ring 140 in the ring-on-ring evaluation apparatus 1 in the vertical direction.

Referring to FIG. 5, as pressure is applied to the surface of the glass article 10 by as much as the area of the rims of the upper and lower rings 130 and 140 during the evaluation of the strength of the glass article 10 by the ring-on-ring evaluation device 1, the area of contact of the glass article 10 and the upper ring 130 and/or the lower ring 140 may be large. The rim of the upper ring 130 may have a width W1 of about 1.56 mm, and the rim of the lower ring 140 may have a width W2 of about 3.4 mm.

Due to the difference in inner diameter between the upper and lower rings 130 and 140, a part of the glass article 10 that is in contact with, and is pressurized by, the upper ring 130 does not coincide with a part of the glass article 10 that is in contact with, and is pressurized by, the lower ring 140.

Also, as the upper ring 130 and/or the lower ring 140 applies pressure to the glass article 10 by as much as the widths W1 and W2, respectively, the surfaces of the glass article 10 may include a plurality of pressurized regions, and as differences arise in the pressure applied to each of the pressurized regions, the pressure applied to an entirety of the glass article 10 may be imbalanced.

Thus, in a case where the glass article 10 is ultrathin, the glass article 10 may be bent in the thickness direction by the pressure applied by the upper ring 130 and/or the lower ring 140 so that curved surfaces may be generated. On the contrary, the upper and lower rings 130 and 140, which apply pressure to the glass article 10, maintain their original shape. Thus, gaps may be defined between the glass article 10 and the upper ring 130 and/or the lower ring 140 so that inclined surfaces may be generated on the glass article 10.

In a case where inclined surfaces are generated on the glass article 10, slip concern area S may be generated in response to the ends of the upper and lower rings 130 and 140 applying pressure to the inclined surfaces on the glass article 10.

Due to the inclined surfaces on the glass article 10, there may be regions where the pressure from the upper ring 130 and/or the lower ring 140 is not applied, and these regions may be defined as slip concern area S.

Due to the presence of the slip concern area S on the glass article 10, the vertical force applied by the upper ring 130 and/or the lower ring 140 to the glass article 10 may not be able to be precisely measured by the ring-on-ring evaluation device 1.

Figure 6:
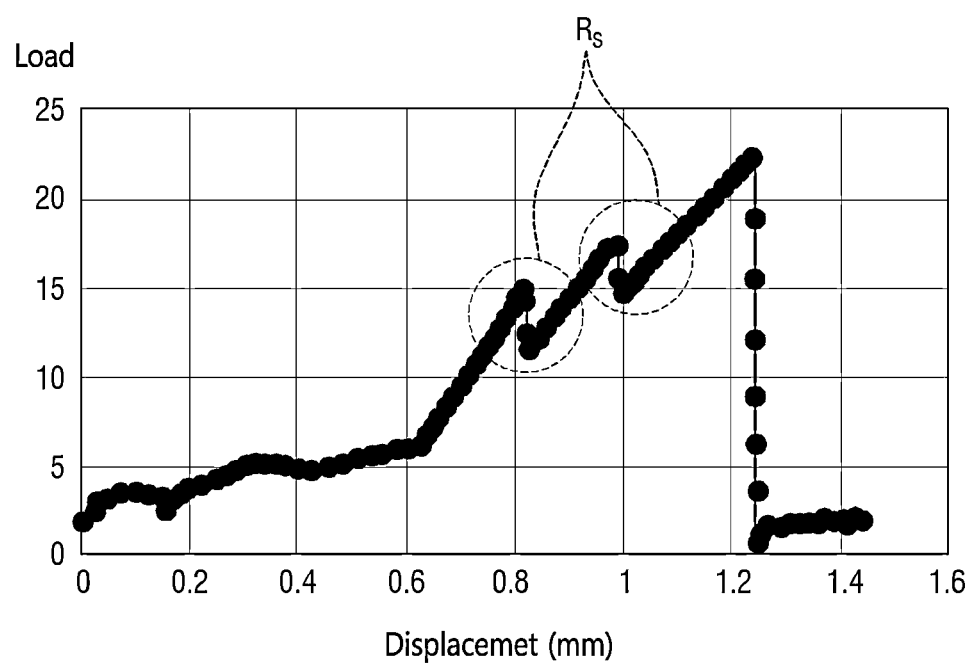
FIG. 6 is a graph showing the relationship between load and displacement, as measured by the ring-on-ring evaluation device of FIG. 5.

FIG. 6 is a graph showing the relationship between load and displacement, as measured by the ring-on-ring evaluation device of FIG. 5.

Referring to FIG. 6, a vertical axis represents the load applied by the ring-on-ring evaluation device 1 to the glass article 10, and a horizontal axis represents the displacement in the direction of the load. However, the disclosure is not limited thereto.

As the load applied by the upper ring 130 to the glass article 10 increases, the displacement of the glass article 10 increases in accordance with the indentation depth of the upper ring 130. The displacement of the glass article 10 refers to the displacement of the glass article 10 in the direction of the load from the upper ring 130.

Referring to FIG. 6, there exist sections RS in a load-displacement curve where the load applied by the upper ring 130 increases and then drops temporarily with a negative slope. The sections RS correspond to the slip concern area S on the glass article 10 where the load from the upper ring 130 is not applied.

Specifically, as the load from the upper ring 130 increases, the displacement of the glass article 10 in the direction of the load from the upper ring 130 tends to increase until encountering the sections RS, which means that the load from the upper ring 130 is applied precisely to the glass article 10.

On the contrary, in the sections RS where the load from the upper ring 130 drops temporarily with a negative slope, the displacement of the glass article 10 in the direction of the load from the upper ring 130 also drops temporarily, even when the load applied by the upper ring 130 to the glass article 10 increases. This means that in the sections RS, as the upper ring 130 applies pressure to the inclined surfaces generated on the glass article 10 so that slips are generated, the load from the upper ring 130 is not precisely applied to the glass article 10.

Referring to FIG. 6, a point where the load-displacement curve begins to drop at a right angle corresponds to the failure load of the glass article 10.

The strength of an ultrathin glass article 10 may be measured with the ring-on-ring evaluation device 1, but due to the presence of slips, failure load measurements obtained by the ring-on-ring evaluation device 1 may be higher than the actual failure load of the glass article 10. Also, as there is a difficulty in determining the correlation between load and displacement, as measured by the ring-on-ring evaluation device 1, the reliability of the evaluation of the strength of the glass article 10 by the ring-on-ring evaluation device 1 may be lowered.

A glass strength evaluation apparatus 2, which is capable of addressing the problems associated with slips generated on the glass article 10 during the measurement of the strength of the glass article 10, will hereinafter be described with reference to FIG. 7.

Figure 7:
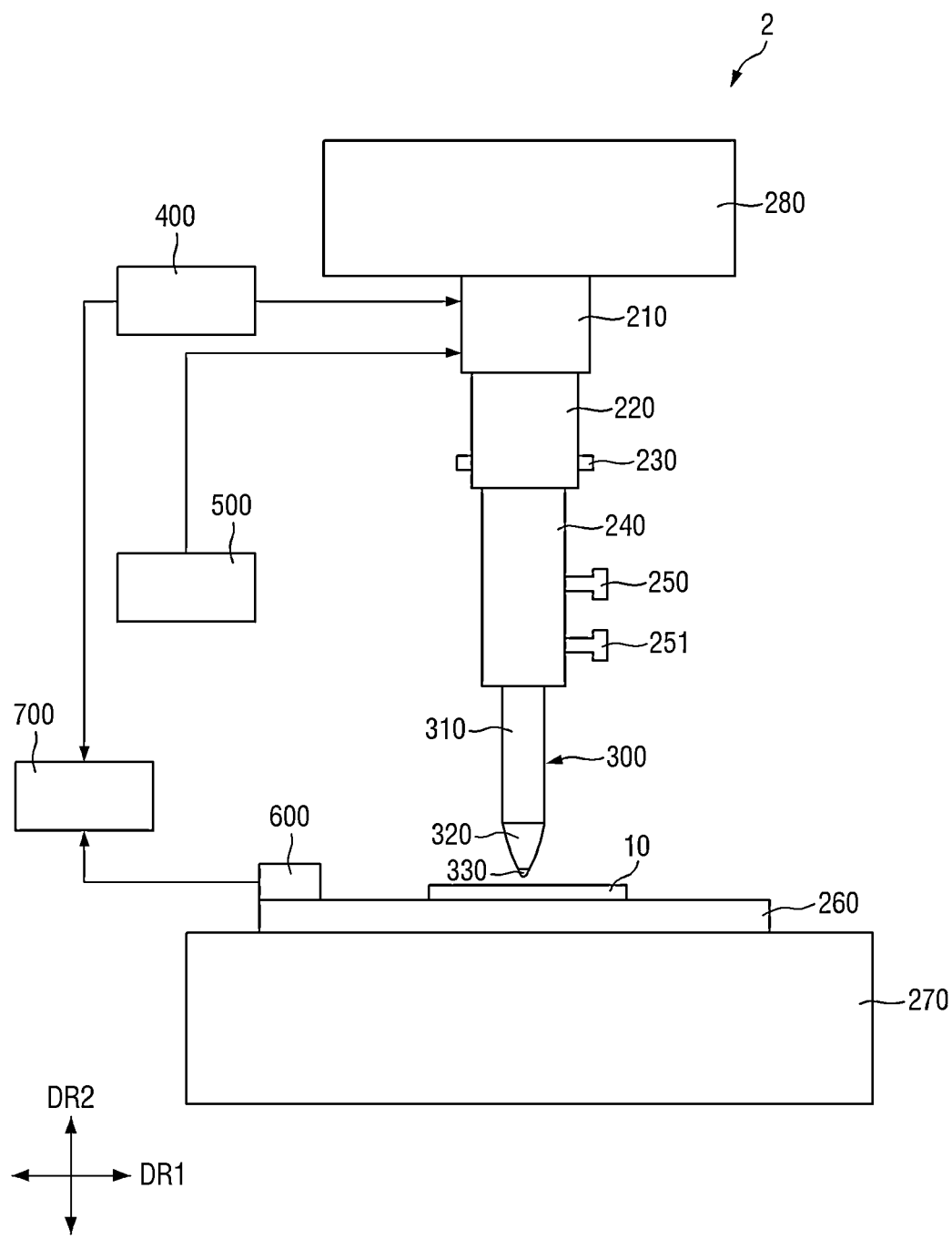
FIG. 7 is a front view of an embodiment of a glass strength evaluation apparatus according to the disclosure.

FIG. 7 is a front view of a glass strength evaluation apparatus according to the disclosure.

Referring to FIG. 7, the glass strength evaluation apparatus 2 differs from the ring-on-ring evaluation device 1 (refer to FIGS. 4 and 5) in that the contact area of an indenter 330 of a press-fitting member 300 and the glass article 10 is smaller than the area of contact of the glass article 10 and the upper ring 130 (refer to FIGS. 4 and 5) and/or the lower ring 140 (refer to FIGS. 4 and 5) of the ring-on-ring evaluation device 1, the glass article 10, which is a target to be tested, is placed on a plate 260 to have an entirety of a bottom surface in contact with the plate 260, and an entirety of the bottom surface of the glass article 10 is supported by the plate 260.

As a reaction to the applying of pressure to the top surface of the glass article 10 by the indenter 330, the plate 260 applies pressure to the bottom surface of the glass article 10 in a first direction DR1, and as a result, points of contact between the top and bottom surfaces of the glass article 10 may coincide with each other.

Accordingly, the indenter 330 may be fixed to the point of contact on the top surface of the glass article 10, and the pressure applied by the indenter 330 to the glass article 10 may be concentrated upon the point of contact on the top surface of the glass article 10 without generating any slips.

When the indenter 330 applies pressure to the top surface of the glass article 10 when the glass article 10 is not disposed on the plate 260, the glass article 10 may be bent in the thickness direction by the pressure applied by the indenter 220, because of not being supported by the plate 260, so that curved surfaces may be generated on the glass article 10.

Even in this case, however, the glass strength evaluation apparatus 2 may properly apply pressure to the glass article 10 without causing any slips because the contact area of the indenter 330 and the glass article 10 is relatively small so that the pressure applied by the glass strength evaluation apparatus 2 may be concentrated upon one arbitrary point on the glass article 10.

The structure of the glass strength evaluation apparatus 2 will hereinafter be described.

For convenience, referring to FIG. 7, a horizontal direction is defined as the first direction DR1, and the vertical direction is defined as a second direction DR2. However, the disclosure is not limited thereto.

Referring to FIG. 7, the glass strength evaluation apparatus 2 may include a load setting circuit 400, a controller 500, a sensor unit 600, a display panel 700, a base 280, a power unit 210, and a coupling unit 220, an upper fixing pin 230, a fixing jig 240, a first lower fixing bolt 250, a second lower fixing bolt 251, the press-fitting member 300, the plate 260, and a support unit 270.

The support unit 270 may be disposed at the bottom of the glass strength evaluation apparatus 2 to support the rest of the glass strength evaluation apparatus 2.

One side of the power unit 210 may be physically connected to the base 280, and the other side of the power unit 210 may be physically connected to the coupling unit 220.

The power unit 210 may vertically move the fixing jig 240, which is physically coupled to the coupling unit 220, in the second direction DR2. In an embodiment, the power unit 210 may use a motor as a moving structure, for example, but the disclosure is not limited thereto.

The coupling unit 220 may be physically coupled to an upper part of the fixing jig 240, and the upper part of the fixing jig 240 may be fixed by the upper fixing pin 230 while being physically coupled to the coupling unit 220. The coupling unit 220 may have a cylindrical shape extending in the second direction DR2.

The fixing jig 240 may have a cylindrical shape extending in the second direction DR2 and may be physically coupled to the press-fitting member 300 such that the second direction DR2 and the lengthwise direction of the press-fitting member 300 may coincide with each other. The shape of the fixing jig 240 is not particularly limited.

The fixing jig 240 and the press-fitting member 300, which is coupled to the fixing jig 240, will be described later.

The load setting circuit 400 may set a vertical load to be applied by the press-fitting member 300 and the descending speed of the press-fitting member 300. Specifically, the load setting circuit 400 may set the rotation speed of the motor of the power unit 210 and may also set the descending speed of the press-fitting member 300 in accordance with the rotation speed of the motor of the power unit 210.

The controller 50 may control the press-fitting member 300's operation of applying a load onto the glass article 10 by moving in the second direction DR2. That is, the controller 500 may control the operation of the power unit 210 such that the press-fitting member 300, which is coupled to the fixing jig 240, may apply a load onto the glass article 10 in accordance with the load or the descending speed set by the load setting circuit 400.

The plate 260 may be disposed on the support unit 270 and may be physically fixed to the support unit 270. The plate 260 may have a flat top surface and may be unitary without any separate surfaces.

The length of the short sides of the plate 260 and the length of the long sides of the plate 260 may be greater than the length of the short sides of the glass article 10 and the length of the long sides of the glass article 10, and an entirety of the glass article 10 may be properly disposed (e.g., mounted) on the plate 260. As no element is interposed between the bottom surface of the glass article 10 and the top surface of the plate 260, the top surface of the plate 260 may be in direct contact with the bottom surface of the glass article 10 and may support an entirety of the bottom surface of the glass article 10.

When the indenter 330 of the press-fitting member 300 is in direct contact with the top surface of the glass article 10 on the plate 260 and applies pressure to the glass article 10, the top surface of the plate 260 may also apply pressure to an entirety of the bottom surface of the glass article 10 in the second direction DR2 such that the glass article 10 may be fixed onto the plate 260.

Accordingly, the shape of the glass article 10 may be well maintained when the indenter 330 of the press-fitting member 300 applies pressure to the glass article 10 on the plate 260.

The sensor unit 600 may be disposed on the plate 260 and may detect the load applied to the glass article 10 and the breakage of the glass article 10, but the disclosure is not limited thereto. The sensor unit 600 may detect various measurement data from the glass strength evaluation apparatus 2.

In response to any breakage being detected from the surfaces of the glass article 10, the sensor unit 600 may display the detected breakages via the display panel 700 and may thus allow a user to remove the glass article 10. Measurement data obtained by the sensor unit 600 such as measurements of the load applied to the glass article 10 and the displacement of the glass article 10 may be displayed via the display panel 700.

The press-fitting member 300, which is coupled to the fixing jig 240, will hereinafter be described with reference to FIGS. 8 through 10.

Figure 8:
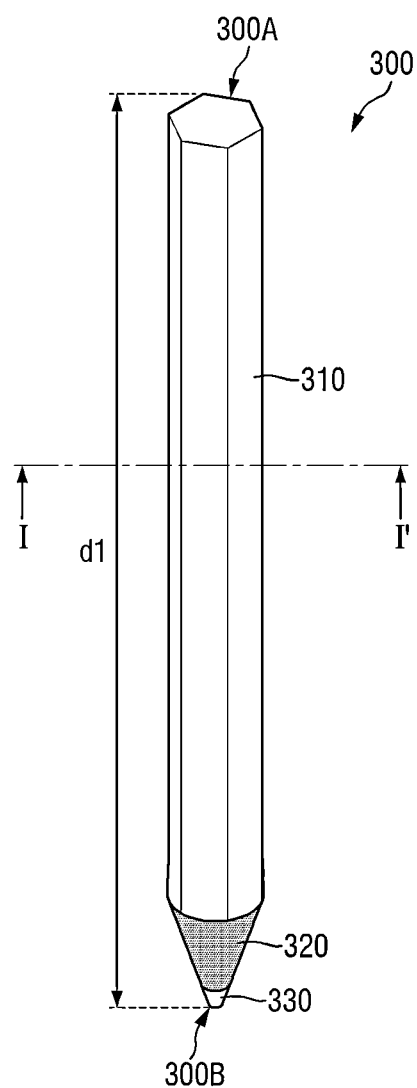
FIG. 8 is a perspective view of the press-fitting member of FIG. 7.

FIG. 8 is a perspective view of the press-fitting member of FIG. 7. FIG. 9 is a cross-sectional view taken along line I-I' of FIG. 8. FIG. 10 is an enlarged cross-sectional view of the indenter of the press-fitting member of FIG. 8.

Figure 10:
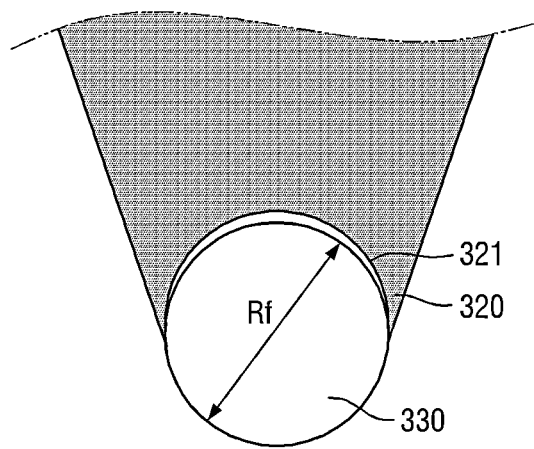
FIG. 10 is an enlarged cross-sectional view of the indenter of the press-fitting member of FIG. 8.

Referring to FIGS. 8 and 10, the press-fitting member 300, which is coupled to the fixing jig 240 of the glass strength evaluation apparatus 2, may include a body portion 310, an indenter cover 320, an indenter support 321, and the indenter 330.

One end of the press-fitting member 300 will hereinafter be also referred to as a base end 300A, the other end of the press-fitting member 300 that is opposite to the base end 300A will hereinafter be also referred to as a front end 300B, a side of the press-fitting member 300 close to the base end 300A will hereinafter be also referred to as a base-end side, and a side of the press-fitting member 300 close to the front end 300B will hereinafter be also referred to as a front-end side.

A length d1 from the base end 300A to the front end 300B of the press-fitting member 300 may be about 149 mm, and the body portion 310 of the press-fitting member 300 may have a length of about 140 mm. However, the disclosure is not limited to this.

Figure 9:
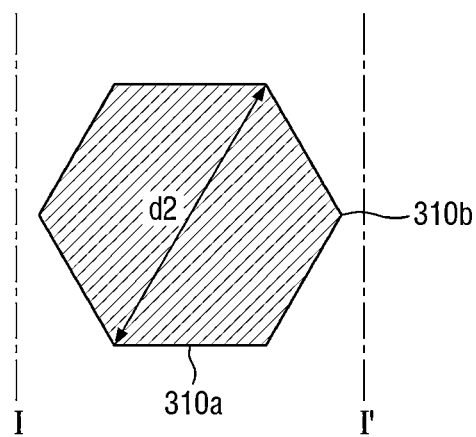
FIG. 9 is a cross-sectional view taken along line I-I' of FIG. 8.

Referring to FIGS. 8 and 9, the body portion 310 may have a regular hexagonal column shape extending from the base end 300A to the front end 300B, and a cut surface of the body portion 310 may have a regular hexagonal shape. The body portion 310 may have flat sides 310a and corners 310b, which are formed or provided by pairs of adjacent flat sides 310a.

Referring to FIG. 9, a length d2 between a pair of opposite corners 310b on the cut surface of the body portion 310 may be about 8 mm, but the disclosure is not limited thereto.

Referring to FIGS. 8 and 10, the indenter cover 320, which is disposed on the front end side of the press-fitting member 300, may have a tapered shape to have a smaller diameter closer to the front end 300B and may fix the indenter 330 by exposing a part of the indenter 330 at the front end 300B.

The indenter cover 320 may include the indenter support 321 to prevent the indenter 330 from being inserted in the opposite direction to the direction in which pressure is applied by the indenter 330 to the glass article 10, and the indenter support 321 may include a curved shape on the inside to receive the indenter 330.

Referring to FIG. 10, the indenter 330, which is partially exposed by the indenter cover 320, may generally have a ball shape or may include at least a part of a ball shape. A diameter Rf of the indenter 330 may be about 0.3 mm to about 1 mm, preferably about 0.7 mm.

When the indenter 330 has a diameter Rf of about 0.3 mm, the indenter 330 may fail to withstand the pressure applied to the glass article 10 and may thus be bent or damaged, and a vertical force applied by the indenter 330 to the glass article 10 may not be able to be accurately evaluated. When the diameter Rf of the indenter 330 exceeds about 1 mm, the slip concern area S may be generated during the measurement of the strength of an ultrathin glass article 10 having a thickness of 100 µm or less.

In a case where the diameter Rf of the indenter 330 is about 0.7 mm, noise that may be generated during the measurement of an ultrathin glass article 10 having a thickness of 100 µm or less may be minimized, and data such as failure load may be precisely measured.

The indenter of the press-fitting member 300 may have a higher Young's modulus, Poisson's ratio, and density than those of the glass article 10 and may thus have a greater rigidity or strength than those of the glass article 10.

Thus, even when the glass article 10 is damaged by the pressure applied by the indenter 330, the indenter 330 is not damaged or deformed, but the shape of the indenter 330 may be maintained, until the glass article 10 is broken.

The indenter 330 may include a wear-resistant chromium alloy (e.g., 100Cr6) and may have a Young's modulus of about 210 gigapascals (GPa), a Poisson's ratio of about 0.3, and a density of about 7800 kilograms per cubic meter (kg/m3), but the disclosure is not limited thereto.

It will hereinafter be described with reference to FIGS. 11 and 12 how the fixing jig 240 is coupled to the other elements of the glass strength evaluation apparatus 2.

Figure 11:
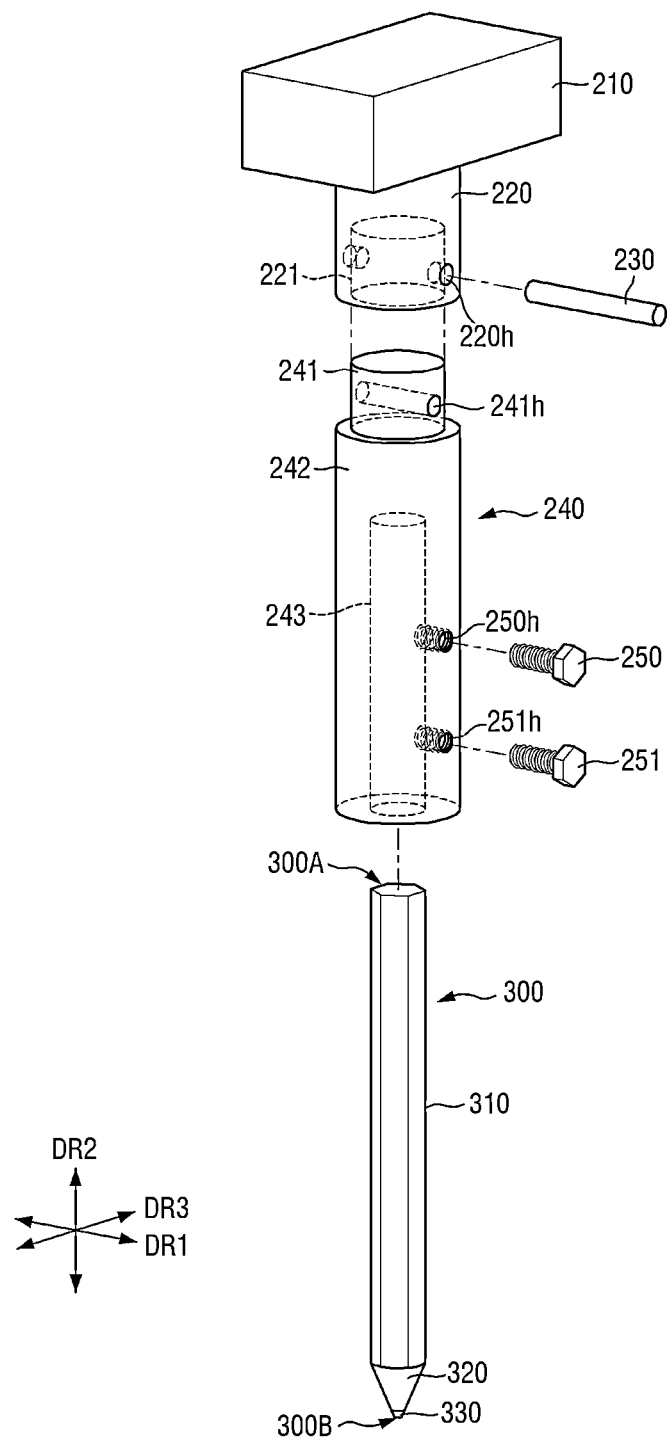
FIG. 11 is an exploded perspective view of the apparatus of FIG. 7.

FIG. 11 is an exploded perspective view of the apparatus of FIG. 7. FIG. 12 is a cross-sectional view of the apparatus of FIG. 7.

Figure 12:
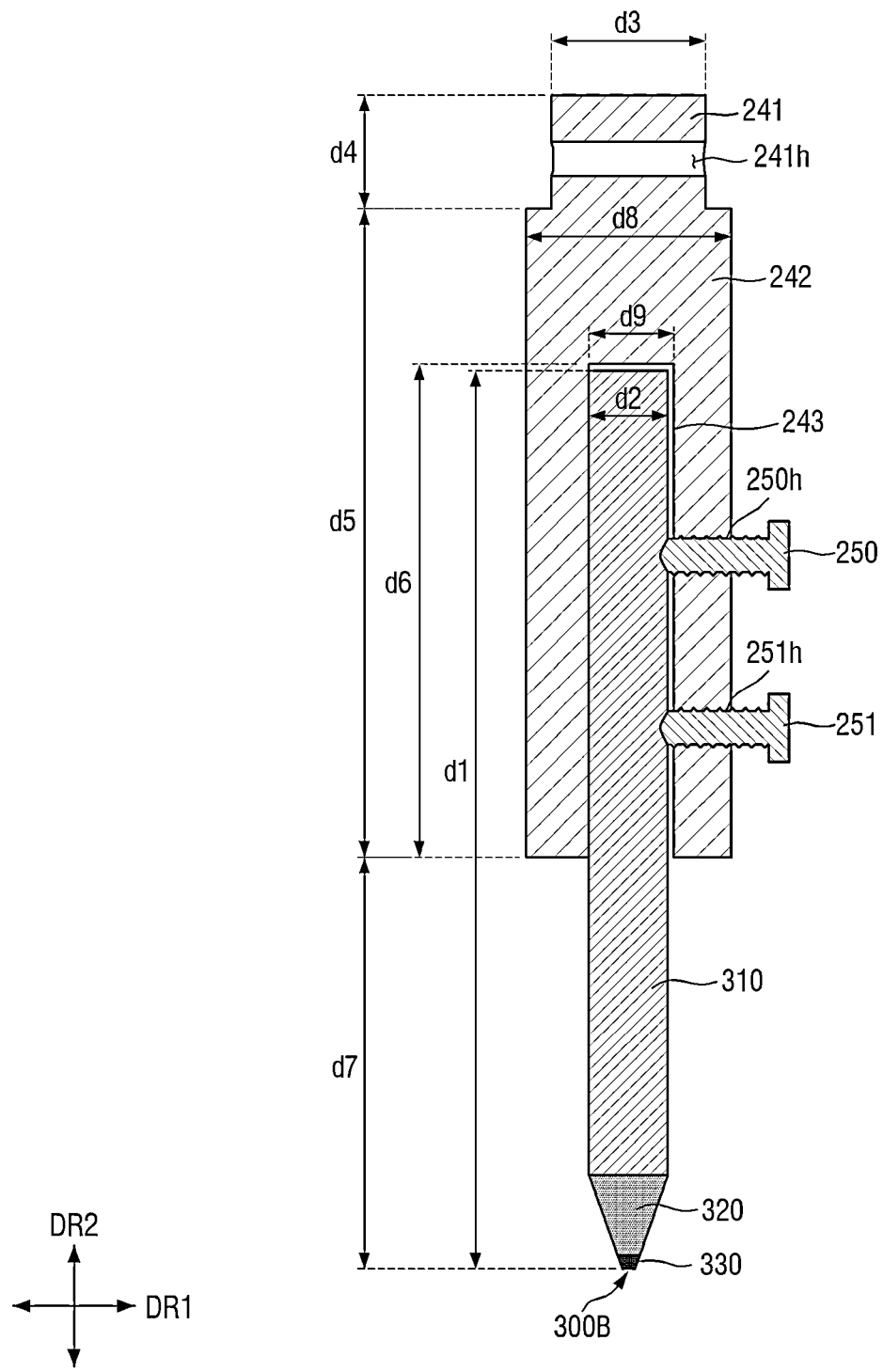
FIG. 12 is a cross-sectional view of the apparatus of FIG. 7.

Referring to FIGS. 11 and 12, the fixing jig 240 may include a coupling (or fastening) head 241 and a body portion 242. A press-fitting member insertion opening 243, a first lower fixing bolt insertion hole 250h, and a second lower fixing bolt insertion hole 251h may be defined in the fixing jig 240.

The press-fitting member insertion opening 243 may be recessed from the bottom of the body portion 242 to extend in an upward direction. The press-fitting member insertion opening 243 may have a diameter d9 greater than the width of the press-fitting member 300, and a length d6, in the second direction DR2, of the press-fitting member insertion opening 243 may be substantially equal to, or greater than, half the length of the body portion 310 of the press-fitting member 300.

When the press-fitting member insertion opening 243 of the fixing jig 240 fails to cover at least half the length of the body portion 310 of the press-fitting member 300, the press-fitting member 300 may be bent, or a slip may be generated on the surface of contact between the indenter 330 of the press-fitting member 300 and the glass article 10.

Thus, a length d7 by which the press-fitting member 300 is exposed on the front-end side of the press-fitting member 300 may vary depending on the length d6, in the second direction DR2, of the press-fitting member insertion opening 243, and as the length d7 decreases, the force of fixing the press-fitting member 300 with the fixing jig 240 may be improved.

The fixing jig 240 is illustrated as exposing the front-end side of the press-fitting member 300 while covering a part of the body portion 310 of the press-fitting member 300, but the disclosure is not limited thereto. In an alternative embodiment, the fixing jig 240 may cover an entirety of the body portion 310 of the press-fitting member 300.

The press-fitting member 300 may be inserted in the press-fitting member insertion opening 243 to be physically detachable from the press-fitting member insertion opening 243. The press-fitting member 300 may be detachably coupled to the press-fitting member insertion opening 243, and other press-fitting members may also be able to be coupled to the fixing jig 240. The press-fitting member 300 may form a tolerance of about 1 mm between the sides of the body portion 310 and the inner sidewall of the press-fitting member insertion opening 243, but the disclosure is not limited thereto.

The first and second lower fixing bolt insertion holes 250h and 251h may be defined in one surface of the body portion 242 of the fixing jig 240 along the second direction DR2, may penetrate the press-fitting member insertion opening 243 in a first horizontal direction intersecting the second direction DR2, from one side of the body portion 242 to be connected to the press-fitting member insertion opening 243, and the second lower fixing bolt insertion hole 251h may be disposed lower the first lower fixing bolt insertion hole 250h.

The first and second lower fixing bolt insertion holes 250h and 251h may include screw grooves on the inner sidewalls thereof, and the first and second lower fixing bolts 250 and 251 may include screw threads corresponding to the thread grooves.

The first and second lower fixing bolts 250 and 251 may be physically coupled to the first and second lower fixing bolt insertion holes 250h and 251h, respectively, by being inserted into the first and second lower fixing bolt insertion holes 250h and 251h, respectively, in the first horizontal direction.

The ends of the first and second lower fixing bolts 250 and 251 coupled to the body portion 242 through the body portion 242 may fix the press-fitting member 300 while being in contact with the flat sides 310a of the body portion 310, and the flat sides 310a of the body portion 310 may adjoint the inner sidewall of the press-fitting member insertion opening 243.

Thus, the press-fitting member 300 may be fixed in the second direction DR2 to precisely face the glass article 10 by controlling the length by which, and/or the angle at which, the first and second lower fixing bolts 250 and 251 are inserted in the first and second lower fixing bolt insertion holes 250h and 251h, respectively, in the first horizontal direction.

Also, even when a pen other than the press-fitting member 300 is inserted in the press-fitting member insertion opening 243 or the press-fitting member 300 is deformed or damaged after multiple experiments, the press-fitting member 300 may still be fixed in the second direction DR2 by controlling the length by which, and/or the angle at which, the first and second lower fixing bolts 250 and 251 are inserted in the first and second lower fixing bolt insertion holes 250h and 251h, respectively, in the first horizontal direction.

The first and second lower fixing bolts 250 and 251 are illustrated as being identical bolts, but the disclosure is not limited thereto. In an alternative embodiment, two or more different fixing bolts may be provided. In an alternative embodiment, the first lower fixing bolt 250 may be disposed on one side of the fixing jig 240, and the second lower fixing bolt 251 may be disposed on the other side of the fixing jig 240.

The coupling head 241 may be connected to the upper end of the body portion 310 of the press-fitting member 300 and may generally have a cylindrical shape extending in the second direction DR2, but the disclosure is not limited thereto.

A length d4, in the second direction DR2, of the coupling head 241 may be less than a length d5, in the second direction DR2, of the body portion 242, and an outer diameter d3 of the coupling head 241 may be less than an outer diameter d8 of the body portion 242.

The coupling head 241 may be inserted in the coupling unit 220, and the coupling head 241 may be received in a head receiving portion 221 of the coupling unit 220.

Upper fixing pin insertion holes 220h may be defined in the coupling unit 220. Specifically, the upper fixing pin insertion holes 220h may include a first upper fixing pin insertion hole, which penetrates the coupling unit 220 in a second horizontal direction, intersecting the vertical direction, from a first side of the coupling unit 220 corresponding to a first side of the coupling head 241 toward the head receiving portion 221, and a second upper fixing pin insertion hole, which penetrates the coupling unit 220 in the second horizontal direction from a second side of the coupling unit 220 corresponding to a second side of the coupling head 241 toward the head receiving portion 221.

The second horizontal direction may coincide with the first horizontal direction or may intersect the first horizontal direction.

The upper fixing pin 230 may be coupled across the upper fixing pin insertion holes 220h and a head fixing pin insertion hole 241h. That is, the upper fixing pin 230 may penetrate the coupling unit 220 through the first upper fixing pin insertion hole, the head fixing pin insertion hole 241h, and the second upper fixing pin insertion hole in the second horizontal direction to fix the upper part of the fixing jig 240.

Referring to FIGS. 11 and 12, the lower end of the body portion 242 may coincide with the lower end of the press-fitting member insertion opening 243, but an upper part of the body portion 242 may extend further than an upper part of the press-fitting member insertion opening 243 in the second direction DR2. Thus, the length d5, in the second direction DR2, of the body portion 242 may be greater than the length d6, in the second direction DR2, of the body portion 242, but the disclosure is not limited thereto. In an alternative embodiment, the length d5, in the second direction DR2, of the body portion 242 may be substantially the same as the length d6, in the second direction DR2, of the body portion 242.

In a case where the press-fitting member 300 having a length d1 of about 149 mm in the second direction DR2 and a width d2 of about 8 mm is coupled to the fixing jig 240, the press-fitting member insertion opening 243 may have a diameter d9 of about 8 mm to about 9 mm and a length d6 of about 70 mm to about 140 mm in the second direction DR2 to maintain a tolerance of about 0.1 centimeter (cm) with the press-fitting member 300.

The lower end of the body portion 242 may coincide with the lower end of the press-fitting member insertion opening 243, the upper part of the body portion 242 may extend further than the upper end of the press-fitting member insertion opening 243 in the second direction DR2, and the length d5, in the second direction DR2, of the body portion 242 may be about 92 mm to about 162 mm.

Accordingly, the length d7 by which the press-fitting member 300 is exposed on the front-end side of the press-fitting member 300 may be about 9 mm to about 79 mm, but the disclosure is not limited thereto.

Figure 13:
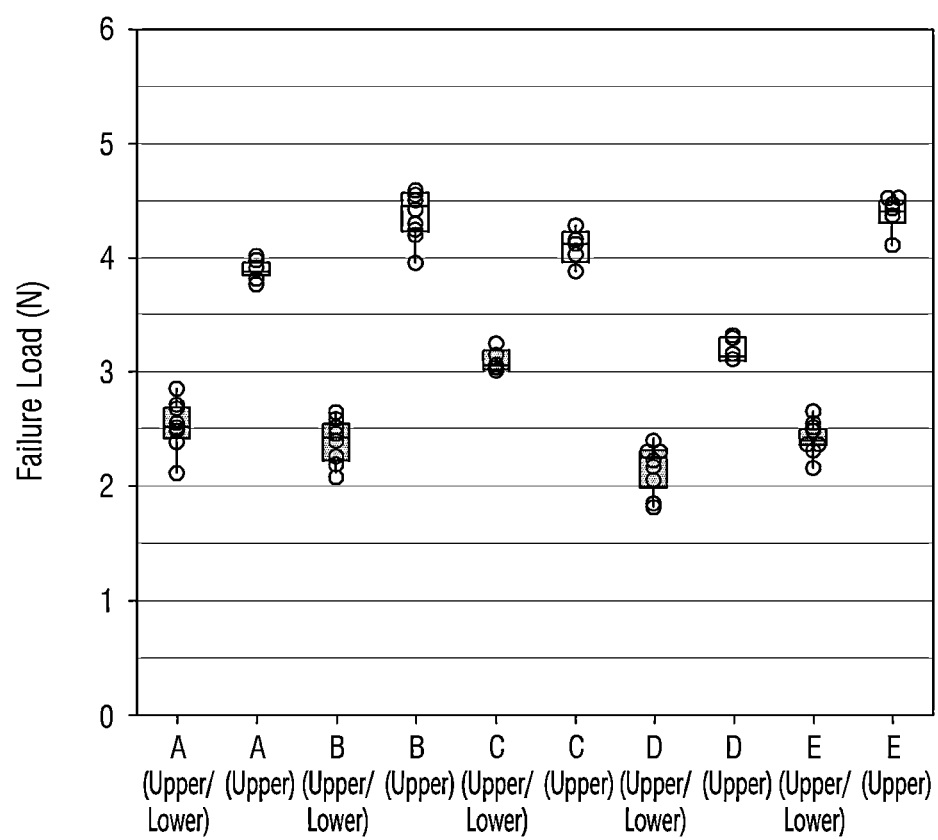
FIG. 13 is a graph showing the relationship between the failure load of the glass article and whether the upper part or both the upper and lower parts of the fixing jig, to which the press-fitting member is coupled, are fixed.

FIG. 13 is a graph showing the relationship between the failure load of the glass article and whether the upper part or both the upper and lower parts of the fixing jig, to which the press-fitting member is coupled, are fixed.

Referring to FIG. 13, a horizontal axis represents samples A, B, C, and D, and a vertical axis represents the failure loads of samples A, B, C, and D for whether the upper part or both the upper and lower parts of the fixing jig 240 are fixed.

The failure loads of samples A, B, C, and D is generally lower when both upper and lower parts of the fixing jig 240, to which the press-fitting member 300, is coupled, are fixed than when only the upper part of the fixing jig 240 is fixed. However, the disclosure is not limited thereto.

As already mentioned above, during the evaluation of the strength of the glass article 10 by the glass strength evaluation apparatus 2, in response to the indenter 330 of the press-fitting member 300 applying pressure to the top surface of the glass article 10 while being in contact with the glass article 10, the top surface of the plate 260 may also apply pressure to the bottom surface of the glass article 10 so that an entirety of the bottom surface of the glass article 10 may be supported by the plate 260 and the points of contact between the glass strength evaluation apparatus 2 and the top and bottom surfaces of the glass article 10 may coincide with each other. Thus, the vertical force applied by the indenter 330 of the press-fitting member 300 may be evaluated differently depending on whether the upper part, the lower part, or both the upper and lower parts of the fixing jig 240, to which the press-fitting member 300 is coupled, are fixed.

Specifically, in a case where the fixing jig 240 includes an upper fixing unit to be fixed by the upper fixing pin 230 but does not include a lower fixing unit to be fixed by the first and second lower fixing bolts 250 and 251, the fixing force for the press-fitting member 300 may weaken. As a result, when the press-fitting member 300 applies pressure vertically to the glass article 10, the indenter 330 may contact the glass article 10 so that slips may be generated.

Accordingly, as the vertical force applied by the indenter 330 of the press-fitting member 300 to the glass article 10 fails to be precisely evaluated, noise may be generated, and thus, failure load measurements provided by the glass strength evaluation apparatus 2 may be higher than the actual failure load of the glass article 10.

On the contrary, in a case where the fixing jig 240 includes both the upper and lower fixing units, the fixing force, in the horizontal direction, for the press-fitting member 300 may be enhanced by the first and second lower fixing bolts 250 and 251, and slips may not be generated on the surface of contact between the indenter 330 and the glass article 10 when the press-fitting member 300 applies pressure vertically to the glass article 10, and the indenter 330 may be fixed onto the glass article 10 while forming a point of contact on the top surface of the glass article 10.

As the press-fitting member 300 may precisely apply pressure to the point of contact on the top surface of the glass article 10 in the second direction DR2 while maintaining its center on the central axis of the fixing jig 240, the vertical force from the indenter 330 may be precisely evaluated.

That is, as illustrated in FIG. 13, in a case where both the upper and lower parts of the fixing jig 240 are fixed, the indenter 330 may apply a load to the glass article 10 without causing noise, and thus, the failure load of the glass article 10 may be measured low.

It will hereinafter be described how the glass strength evaluation apparatus 2 evaluates the strength of the glass article 10 will hereinafter be described.

Figure 14:
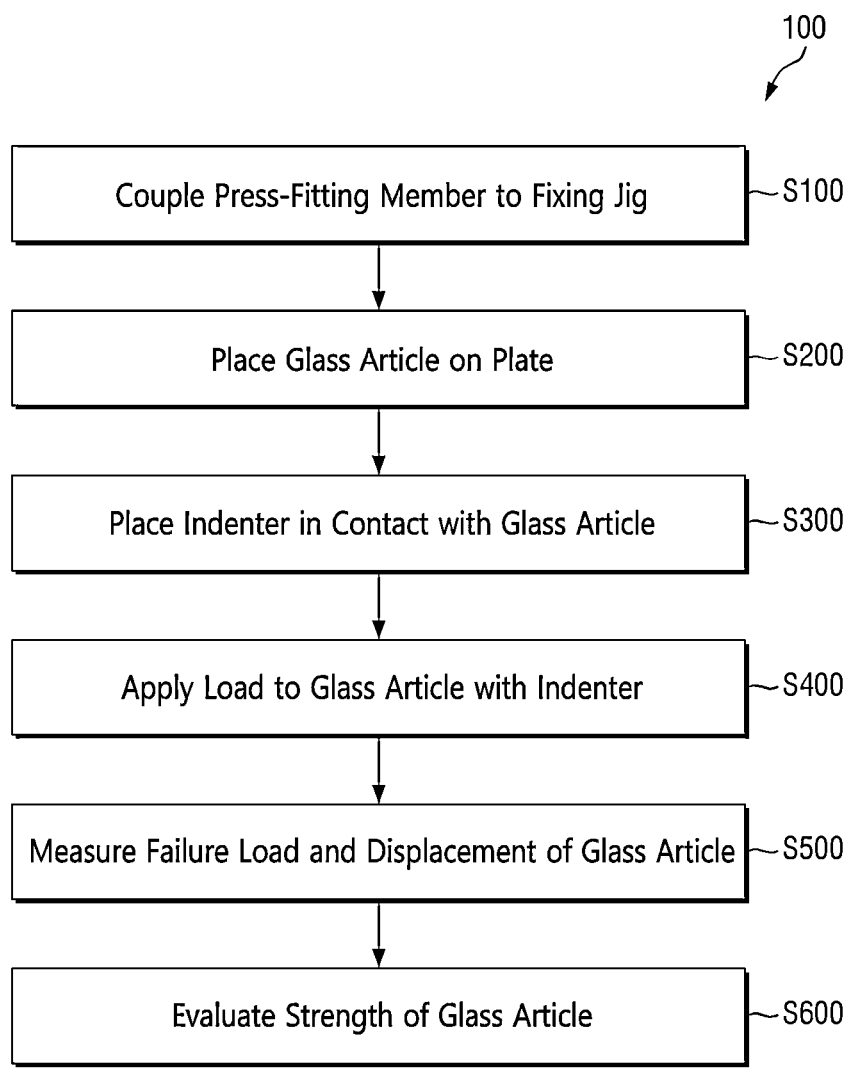
FIG. 14 is a flowchart illustrating an embodiment of a glass strength evaluation method according to the disclosure.
Figure 15:
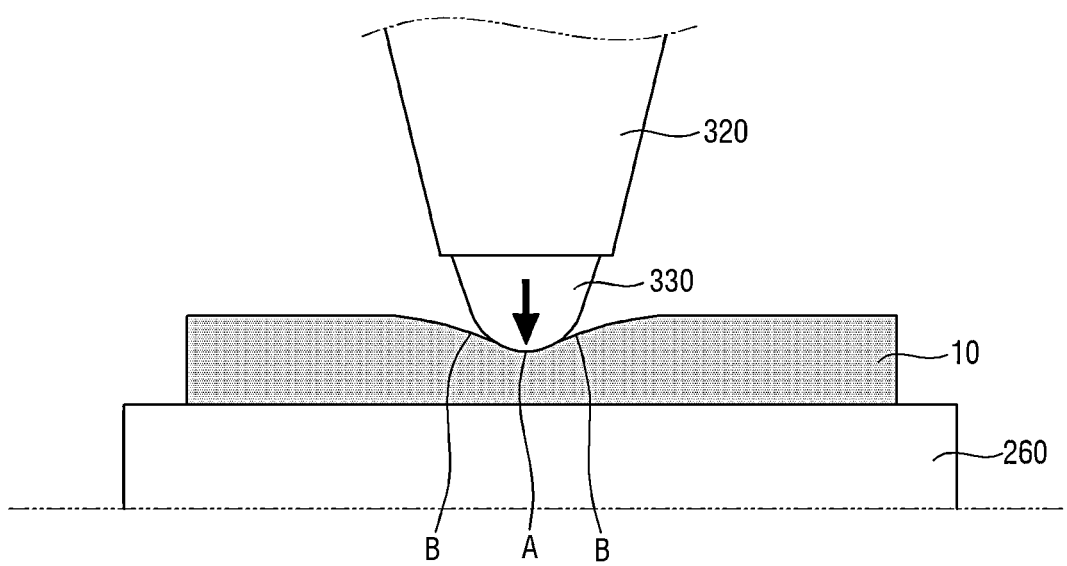
FIGS. 15 through 17 are cross-sectional views illustrating the glass strength evaluation method.
Figure 16:
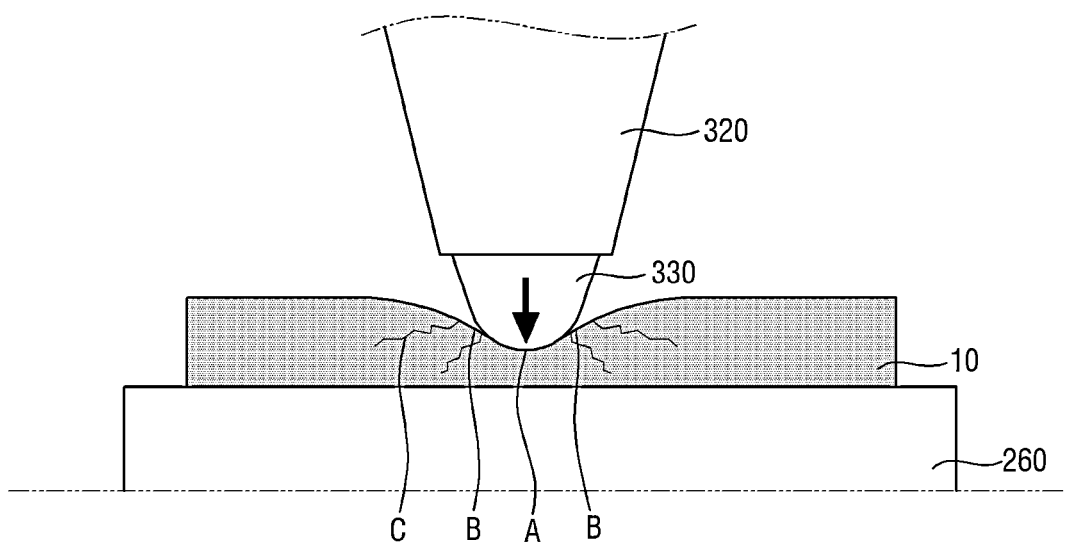
Figure 17:
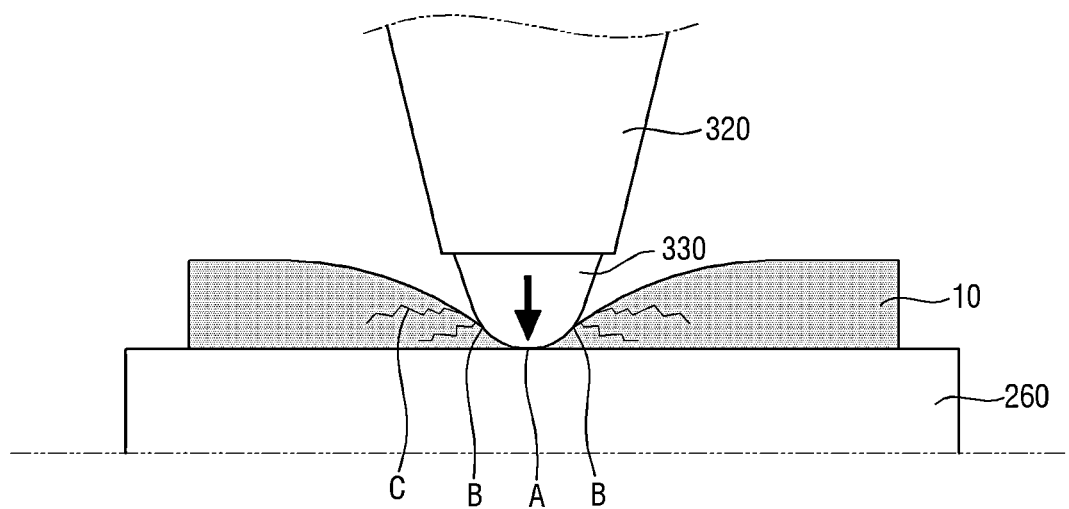
Figure 18:
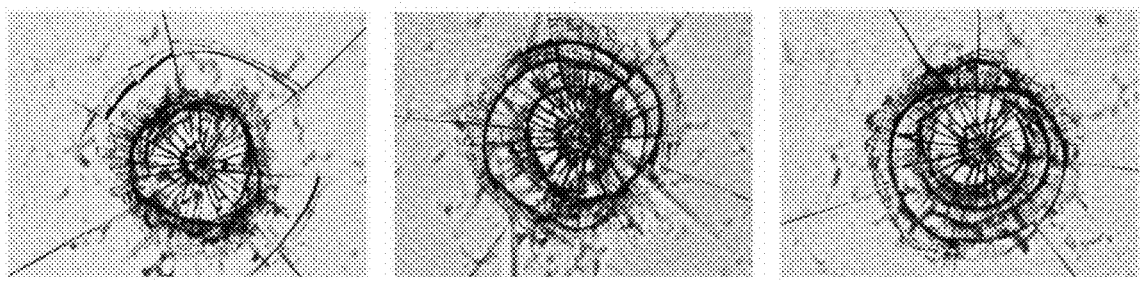
FIG. 18 shows photographs of the surface of a glass article yet to be broken.

FIG. 14 is a flowchart illustrating a glass strength evaluation method according to the disclosure. FIGS. 15 through 17 are cross-sectional views illustrating the glass strength evaluation method. FIG. 18 shows photographs of the surface of a glass article yet to be broken.

Referring to FIG. 14, the press-fitting member 300 is coupled to the fixing jig 243 (S100).

The operation S100 may include selecting the press-fitting member 300, which is to be coupled to the fixing jig 240 of the glass strength evaluation apparatus 2, and determining whether the press-fitting member 300 inserted in the press-fitting member insertion opening 243 is fixed vertically.

When there are multiple glass articles 10 to be evaluated, the operation S100 may further include determining whether a first glass article 10 is broken, retrieving the first glass article 10, and separating a first press-fitting member 300 from the fixing jig 240.

The press-fitting member 300, which is coupled to the fixing jig 240, may be a commercially available pen and may further include an ink storage.

The length and the width of the press-fitting member 300 may vary, and the shape of the body portion 310 of the press-fitting member 300 is not particularly limited. In an alternative embodiment, a press-fitting member 300 having curved surfaces may be provided. Also, a press-fitting member 300 designated for the fixing jig 240 may be fabricated and may then be coupled to the fixing jig 240.

The press-fitting member 300, which is for evaluating the strength of the glass article 10, may vary depending on the thickness and the surface state of the glass article 10 and the number of glass articles 10. The diameter Rf of the indenter 330 at the front end 300B of the press-fitting member 300 may be about 0.3 mm to about 1.0 mm, preferably about 0.7 mm, but the disclosure is not limited thereto.

When the press-fitting member 300, coupled to the fixing jig 240, is not precisely fixed in the second direction DR2, noise may be generated during the evaluation of the strength of the glass article 10, and as a result, the reliability of measurement data may be degraded.

The precision of the fixing of the press-fitting member 300 in the second direction DR2 may be enhanced by identifying whether the press-fitting member 300, inserted in the press-fitting member insertion opening 243, is fixed in the second direction DR2 and sophisticatedly controlling the length by which, and/or the angle at which, the first and second lower fixing bolts 250 and 251 are inserted in the first and second lower fixing bolt insertion holes 250h and 251h, respectively, of the fixing jig 240 in the first horizontal direction, and thus, the reliability of measurement data provided by the glass strength evaluation apparatus 2 may be improved.

Thereafter, the glass article 10, which is a target to be tested, is disposed on one surface (e.g., the top surface) of the plate 260 to face the indenter 330 (S200).

The plate 260 may include a stainless material. A method to fix the glass article 10 onto the plate 260 is not particularly limited. The glass article 10, which is disposed on the plate 260, may be an ultrathin glass article having a thickness of about 50 µm to about 100 µm. The size of the glass article 10 may be smaller than the size of the plate 260 in a plan view, but the disclosure is not limited thereto. In an alternative embodiment, the size of the glass article 10 may be substantially the same as, or greater than, the size of the plate 260 in a plan view.

Thereafter, the indenter 330 of the press-fitting member 300 is placed in contact with the top surface of the glass article 10 (S300).

As the power unit 210 is moved in a downward direction by the controller 500, the fixing jig 240, connected by the coupling unit 220 to the power unit 210, is also moved in the downward direction, and the indenter 330 of the press-fitting member 300, coupled to the fixing jig 240, is placed in contact with the top surface of the glass article 10. The location of the point of contact between the indenter 330 of the press-fitting member 300 and the glass article 10 is not particularly limited as long as it falls on the top surface of the glass article 10.

Thereafter, the indenter 330 of the press-fitting member 300, coupled to the fixing jig 240, applies a load to the top surface of the glass article 10 in the second direction DR2 (S400).

The operation S300 may include increasing the load applied by the indenter 330 based on the load and the descending speed set by the load setting circuit 400 based on the thickness of the glass article 10.

The speed of loading or unloading the indenter 330, i.e., the descending speed of the press-fitting member 300, is about 0.1 millimeter per minute (mm/min), and it takes about 10 seconds to about 15 seconds to completely break the glass article 10.

Referring to FIG. 15, when the indenter 330 of the press-fitting member 300 applies a load to the top surface of the glass article 10, the glass article 10 may be elastically deformed in the middle of the surface of contact between the indenter 330 and the top surface of the glass article 10 (as indicated by "A") and may be bent on opposite sides of the surface of contact between the indenter 330 and the top surface of the glass article 10 (as indicated by "B").

The indenter 330, which is exposed by the indenter cover 320 of the press-fitting member 300, has a ball shape, and even when the surface of contact between the indenter 330 and the glass article 10 is too small and is thus deformed, any deformation of the glass article 10 may occur along the shape of the surface of the indenter 330, and thus, the indenter 330 may be fixed onto the surface of contact between the indenter 330 and the top surface of the glass article 10, forming a point of contact on the top surface of the glass article 10.

As the point of contact on the top surface of the glass article 10 and a point of contact on the bottom surface of the glass article 10 coincide with each other and pressure is applied to an entirety of the bottom surface of the glass article 10 by the plate 260, the bottom surface of the glass article 10 is not curved or bent.

As illustrated in FIG. 15, when a vertical load applied by the indenter 330 to the top surface of the glass article 10 is increased by the load setting circuit 400, the displacement, in the direction of the load, of the glass article 10 may increase in accordance with the indentation depth of the indenter 330.

Referring to FIGS. 16 and 17, when the vertical load from the indenter 330 continues to be increased, cracks C are generated in the glass article 10, and eventually, the glass article 10 is broken. The broken glass article 10 may include parts that have not received the load applied by the indenter 330, and the indenter 330 may penetrate through the glass article 10 in the thickness direction to apply a load to the surface of the plate 260.

Referring to FIG. 18, as the indenter 330 is fixed onto the top surface of the glass article 10 while forming a point of contact on the top surface of the glass article 10, the vertical load from the indenter 330 may be concentrated upon the point of contact on the top surface of the glass article 10. As a result, the cracks C mostly occur around the point of contact on the top surface of the glass article 10 and may include concentric cracks around the point of contact on the top surface of the glass article 10 and linear cracks extending from the point of contact on the top surface of the glass article 10 to the sides of the glass article 10.

In a case where the diameter Rf of the indenter 330 is about 0.7 mm, the point of contact between the indenter 330 and the top surface of the glass article 10 may have a diameter of about 0.4 mm before the article 10 is broken by the indenter 330, but the disclosure is not limited thereto.

In this manner, the load applied to the glass article 10 when the glass article 10 is broken and the displacement of the glass article 10 in the direction of the load are measured (S500).

The operation S500 may include sensing the breakage of the glass article 10 with the sensor unit 600, which is installed in the plate 260, and identifying the load set by the load setting circuit 400 as a failure load when the glass article 10 is broken.

The measurement of the failure load and the displacement of the glass article 10 by the glass strength evaluation apparatus 2 is performed multiple times, e.g., 12 times, and the resulting failure load and displacement measurements are averaged. This type of measurement data is displayed by the display panel 700.

Figure 19:
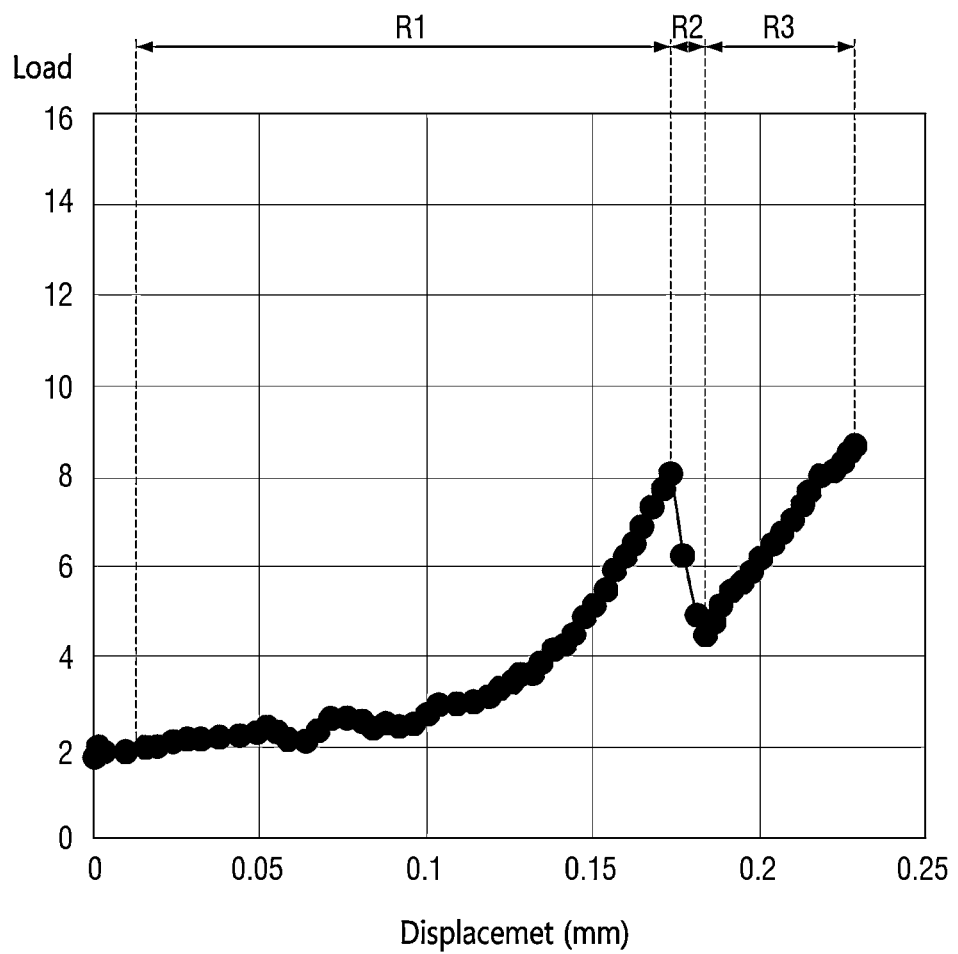
FIG. 19 is a graph showing the relationship between the load applied by the press-fitting member and the displacement, in the direction of the load, of the glass article.

FIG. 19 is a graph showing the relationship between the load applied by the press-fitting member 300 and the displacement, in the direction of the load, of the glass article 10.

Referring to FIG. 19, a horizontal axis represents the displacement of the glass article 10 in the direction of the load applied to the glass article 10, and a vertical axis represents the load applied by the indenter 330 to the glass article 10. When the strength of the glass article 10 is high, the glass article 10 may be broken by a large load, but when the strength of the glass article 10 is low, the glass article 10 may be broken by a small load. Thus, the strength of the glass article 10 may be evaluated based on the displacement-load curve of the glass article 10. Also, the rigidity of the glass article 10 may be evaluated based on the slope of the displacement-load curve of the glass article 10.

Specifically, a section R1 shows the variation of the displacement of the glass article 10, measured by the glass strength evaluation apparatus 2, in accordance with the load set by the load setting circuit 400, until the glass article 10 is broken. In the section R1, as the load applied by the indenter 330 to the glass article 10 increases, the displacement of the glass article 10 in the direction of the load increases in accordance with the indentation depth of the indenter 330 into the top surface of the glass article 10. That is, as the glass article 10 has a predetermined thickness and strength, the displacement of the glass article 10 in the direction of the load continues to increase as long as the load applied by the indenter 330 increases.

Also, in the section R1, no slips are generated on the top surface of the glass article 10 when the indenter 330 applies pressure to the top surface of the glass article 10. Thus, a vertical load from the indenter 330 may be applied precisely onto the top surface of the glass article 10, and thus, any temporary drops in the load from the indenter 330 do not appear in the section R1.

In a section R2, unlike in the section R1, the load from the indenter 330 decreases because a glass article 10 having a rigidity greater than that set by the glass strength evaluation apparatus 2 may maintain its shape, even when a predetermined load or greater is applied thereto, whereas a glass article 10 having a rigidity less than that set by the glass strength evaluation apparatus 2 may not be able to maintain its shape but may be broken upon receiving the predetermined load or greater.

As illustrated in FIG. 19, the load applied by the indenter 330 begins to decrease with a negative slope at the beginning of the section R2, and the load applied at the beginning of the section R2 may be measured as a failure load.

In a section R3, the load applied by the indenter 330 to the top surface of the glass article 10 begins to increase again because the glass article 10 is broken so that the indenter 330 penetrates through the glass article 10 in the thickness direction and begins to apply a load to the plate 260 below the glass article 10.

The sections R1 and R2 are sections from which result values relevant to the evaluation of the strength of the glass article 10 by the glass strength evaluation apparatus 2 may be derived, and the section R3 is a section showing the result of applying pressure to the plate 260 below the glass article 10 and may be irrelevant to the evaluation of the strength of the glass article 10. Accordingly, as temporary drops in the load applied by the indenter 330 or slips do not occur in the section R1, the vertical load applied to the glass article 10 may be precisely evaluated.

The strength of the glass article 10 is evaluated by measuring the failure load and the displacement of the glass article 10 (S600).

As already mentioned above, the strength of the glass article 10 may be evaluated based on the displacement-load graph of the glass article 10, and the rigidity of the glass article 10 may be evaluated based on the slope of the load-displacement curve of the glass article 10.

Other embodiments of the disclosure will hereinafter be described. Like reference numerals indicate like elements throughout the disclosure, and thus, descriptions thereof will be omitted or simplified.

Figure 20:
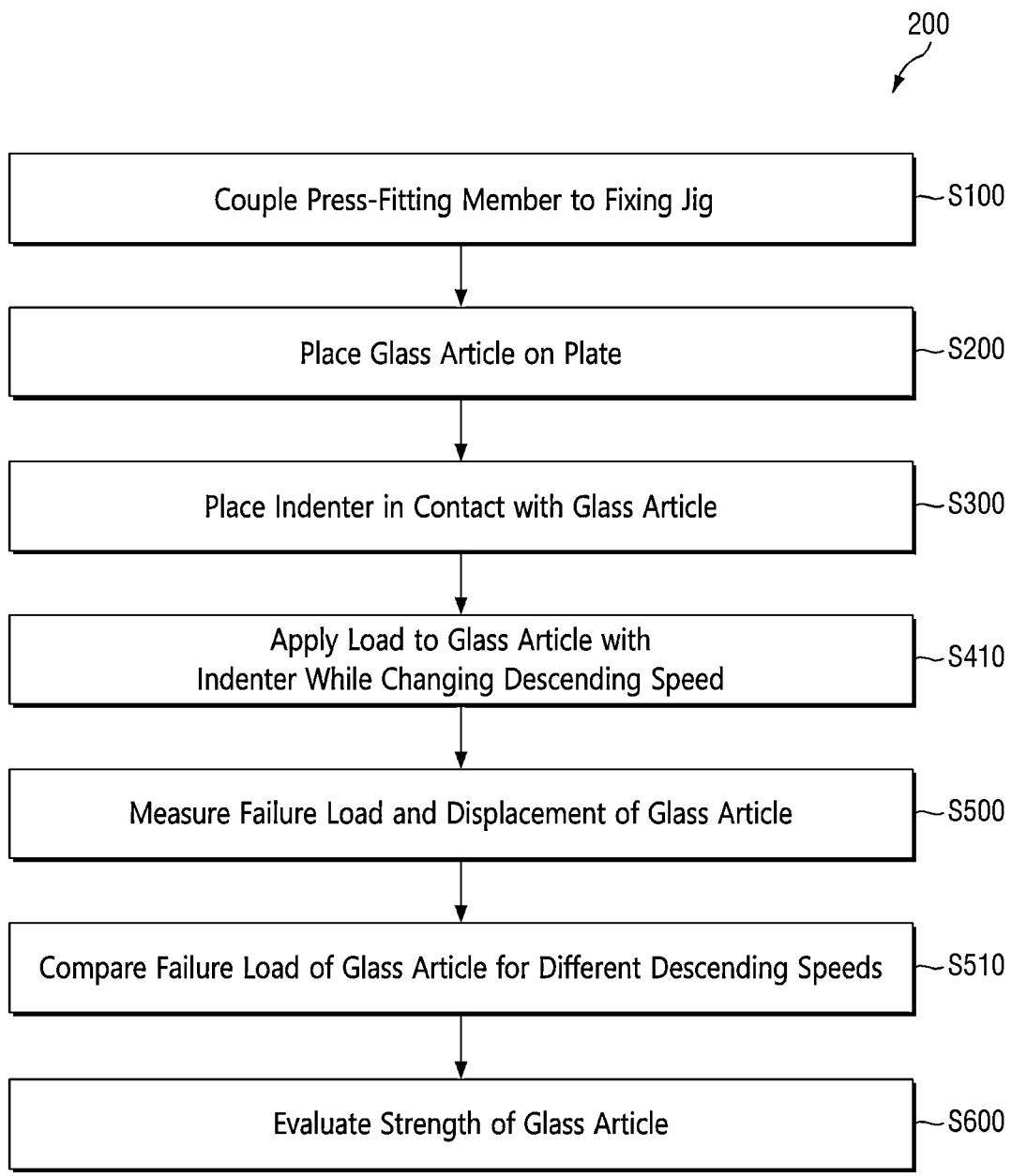
FIG. 20 is a flowchart illustrating an embodiment of a glass strength evaluation method according to the disclosure.
Figure 21:
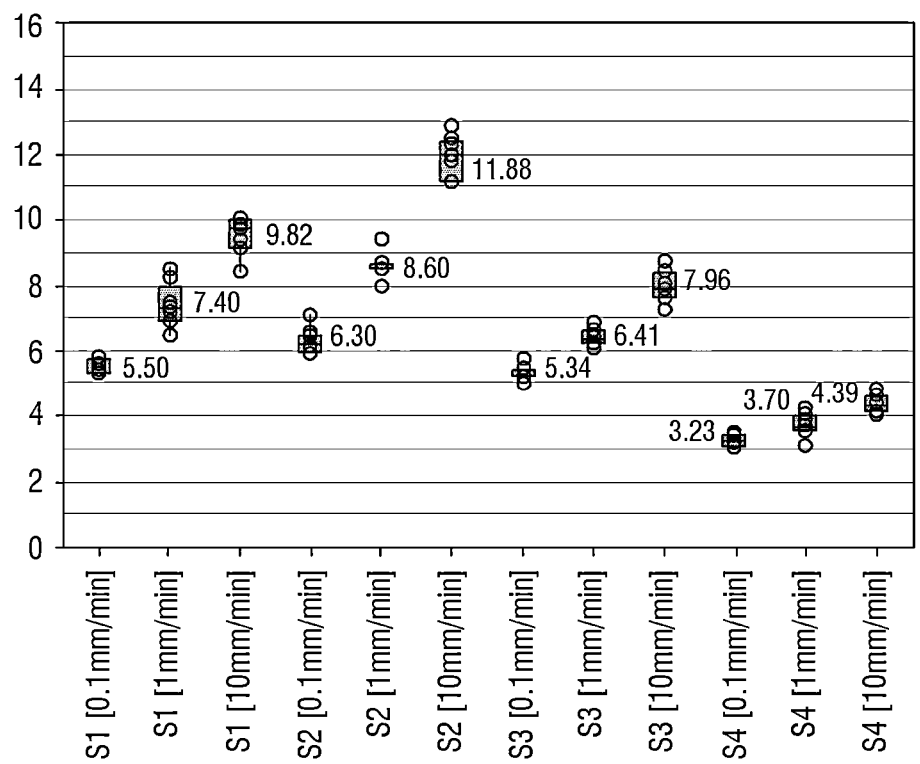
FIG. 21 is a graph showing failure loads for different descending speeds.

FIG. 20 is a flowchart illustrating a glass strength evaluation method according to the disclosure. FIG. 21 is a graph showing failure loads for different descending speeds.

Referring to FIGS. 14 and 20, the glass strength evaluation method 200 differs from the glass strength evaluation method 100 in that it further includes, after placing the press-fitting member 300 in contact with a glass article 10 (S300), applying a load to the glass article 10 while changing the descending speed of the glass strength evaluation apparatus 2 for the glass article 10 (S410) and comparing the failure load of the glass article 10 for different descending speeds (S510).

Specifically, the glass strength evaluation method 200 may evaluate the strength of the glass article 10 by changing the descending speed set by the load setting circuit 400 of the glass strength evaluation apparatus 2.

In S410, the descending speed of the glass strength evaluation apparatus 2 may be one of 0.1 mm/min, 1.0 mm/min, and 10 mm/min when applying a load to a glass article 10.

The failure load of the glass article 10 may vary depending on the descending speed of the glass strength evaluation apparatus 2. As already mentioned above, as the strength of the glass article 10 is proportional to the failure load of the glass article 10, the strength of the glass article 10 may be compared for different failure loads for different descending speeds.

The glass strength evaluation method 200 may evaluate a plurality of glass articles 10. In an embodiment, the plurality of glass articles 10 may include first through fourth samples S1 through S4, for example. Not-slimmed glass articles 10 may be designated as the first through third samples S1 through S4, and a slimmed glass article 10 may be designated as the fourth sample S4. Thus, the first through third samples S1 through S3 may have a different surface state from the fourth sample S4.

S510 may include measuring the failure load of each of the first through fourth samples S1 through S4 while changing the descending speed of the glass strength evaluation apparatus 2 from 0.1 mm/min to 1.0 mm/min to 10 mm/min and comparing the failure loads of the first through fourth samples S1 through S4 for each given descending speed. That is, the first through fourth samples S1 through S4 may have different failure loads for each given descending speed, and this will hereinafter be described later with reference to FIG. 21.

FIG. 21 is a graph showing the failure loads of each of the first through fourth samples S1 through S4 for different descending speeds. Referring to FIG. 21, a horizontal axis represents the descending speed of the glass strength evaluation apparatus 2 for each of the first through fourth samples S1 through S4, and a vertical axis represents the failure load of each of the first through fourth samples S1 through S4 for each given descending speed. However, the disclosure is not limited thereto.

Referring to FIG. 21, as the descending speed of the glass strength evaluation apparatus 2 becomes greater, the failure loads of the first through fourth samples S1 through S4 become greater. That is, as the descending speed of the glass strength evaluation apparatus 2 increases, the failure loads of the first through fourth samples S1 through S4 tend to diverge in a positive direction.

Also, as the descending speed of the glass strength evaluation apparatus 2 becomes greater, the differences between the failure loads of the first through fourth samples S1 through S4 become greater. As a result, the failure loads of the first through fourth samples S1 through S4 may not be able to be properly compared.

Thus, the failure loads of the first through fourth samples S1 through S4 may be properly compared when the descending speed of the glass strength evaluation apparatus 2 is set to 0.1 mm/min. Also, the rigidities of glass articles 10 having different surface states may be properly evaluated by a low-adhesive evaluation method.

Experimental examples will hereinafter be described.

Experimental Example 1: Descending Speed of Glass Strength Evaluation Apparatus

The descending speed of the glass strength evaluation apparatus 2, which was used in the glass strength evaluation method 100, was measured. The descending speed of the glass strength evaluation apparatus 2 was maintained at 0.1 mm/min, 1 mm/min, or 10 mm/min for each of the first through fourth samples S1 through S4, and the normal distribution of each descending speed was verified based on the standard deviation and the Weibull p-value of each descending speed. The result is as shown in Table 1 below. Also, descending speeds was set by comparing ranges of loading rates in accordance with the ASTM C 1499-09 standard.

TABLE 1

| Speed (mm/min) | 0.1 | 1 | 10 |
| --- | --- | --- | --- |
| Standard Deviation | 0.206 | 0.389 | 0.655 |
| P Value | 0.197 | 0.191 | 0.194 |

Referring to Table 1, as the descending speed of 1 mm/min or 10 mm/min has a smaller standard deviation and Weibull P value than the descending speed of 0.1 mm/min, the descending speed of the glass strength evaluation apparatus 2 may preferably be set to 0.1 mm/min.

A setting was made that it would take 15 seconds to completely break each sample. The descending speed of the glass strength evaluation apparatus 2 may preferably be set to 1 mm/min, rather than to 0.1 mm/min or 10 mm/min, in consideration of the evaluation speed. However, the descending speed of the glass strength evaluation apparatus 2 may more preferably be set to be 0.1 mm/min in consideration of the thickness of each sample and the difference between the pressure applied per unit area by the glass strength evaluation apparatus 2 and the pressure applied per unit area by the ring-on-ring evaluation device 1.

Experimental Example 2: Measurement of Failure Loads for Different Descending Speeds The failure loads of the first through third samples S1 through S3, which are prepared by a direct forming process, and the failure load of the fourth sample S4, which was prepared by a slimming process, were measured. Specifically, the first through fourth samples S1 through S4 were placed on a stainless plate, and pressure was applied to each of the first through fourth samples S1 through S4 with the indenter 330 of the press-fitting member 300, which has a diameter of about 0.7 mm, while changing the descending speed of the apparatus from 0.1 mm/min to 1 mm/min to 10 mm/min. The failure loads of the first through fourth samples S1 through S4 were measured eight times. Then, the relationship between the surface states of the first through fourth samples S1 through S4 and the failure loads of the first through fourth samples S1 through S4 was determined based on the averages of the measured failure loads, and the result is as shown in Table 2 below. FIG. 21 shows the relationship between descending speed and failure load.

TABLE 2

|  |  | Type | | | |
|---|---|---|---|---|---|
|  |  | S1 | S2 | S3 | S4 |
|  | Process | Direct Forming (Down Draw) | | | Slimming |
| Failure | 0.1 mm/min | 5.50 | 6.30 | 5.34 | 3.23 |
| Load (N) | 1 mm/min | 7.40 | 8.60 | 6.41 | 3.70 |
|  | 10 mm/min | 9.82 | 11.88 | 7.96 | 4.39 |

Referring to FIG. 21 and Table 2, glass articles 10 obtained by the direct forming process, i.e., the first through third samples S1 through S3, have a greater failure load than that of a glass article 10 obtained by the slimming process, i.e., the fourth sample S4, and this means that the surface state of a sample, resulting from how to prepare the sample, affects the failure load of the sample. Also, referring to FIG. 21 and Table 2, the differences between the failure loads of the first through samples S1 through S4 are smallest when the descending speed of the glass strength evaluation apparatus 2 is 0.1 mm/min.

Experimental Example 3: Comparison with Other Test Methods

The failure heights and the failure loads of the first through third samples S1 through S3, which were prepared by the direct forming process, and the failure height and the failure load of the fourth sample S4, which was prepared by the slimming process, were measured using each of a pen drop test ("PDT") method and a crack initiation load ("CIL") test method, and the results of the measurement are compared with those from the glass strength evaluation method 200, as shown in Table 3 below.

TABLE 3

|  | Type |  | S1 | S2 | S3 | S4 |
|---|---|---|---|---|---|---|
|  | Process |  | Direct Forming (Down Draw) | | | Slimming |
| Failure Load (N) | CIL (N) | Direct Forming | 1.5 | 2.5 | 1.0 | — |
|  |  | (Slimming) | (1.0) | (2.5) | (0.5) | (1.5) |
|  | POP (N) | 0.1 mm/min | 5.50 | 6.30 | 5.34 | 3.23 |
|  |  | 1 mm/min | 7.40 | 8.60 | 6.41 | 3.70 |
|  |  | 10 mm/min | 9.82 | 11.88 | 7.96 | 4.39 |
|  | PDT (cm) | Direct Forming | 5.0 | 5.7 | 5.0 | — |
|  |  | (Slimming) | — | — | — | (1.5) |

Referring to Table 3, test results from the PDT method and the CIL test method show that the first through third samples S1 through S3, which were prepared by the direct forming process, have a greater failure height and load than those of the fourth sample S4, which was prepared by the slimming process, and this coincides with test results from the glass strength evaluation method 200.

Therefore, the test results from the PDT method and the CIL test method may be estimated using the glass strength evaluation method 200.

In concluding the detailed description, those skilled in the art will appreciate that many variations and modifications may be made to the preferred embodiments without substantially departing from the principles of the disclosure. Therefore, the disclosed preferred embodiments of the disclosure are used in a generic and descriptive sense only and not for purposes of limitation.

What is claimed is:

1. A glass strength evaluation apparatus for testing a glass article, the glass strength evaluation apparatus comprising:
   a support unit;
   a plate disposed on the support unit and including a surface on which the glass article, which is a target to be tested, is disposed;
   a fixing jig disposed on the plate, the fixing jig comprising:
      a body portion which extends in a vertical direction and through which lower fixing bolt insertion holes penetrate in a first horizontal direction intersecting the vertical direction; and
      lower fixing bolts which are coupled into the lower fixing bolt insertion holes; and
   a power unit which lifts up or down the fixing jig in the vertical direction toward the surface of the plate,
   wherein
   a press-fitting member insertion opening is recessed from a bottom of the body portion to extend in an upward direction, and is extended to the lower fixing bolt insertion holes.

2. The glass strength evaluation apparatus of claim 1, wherein the lower fixing bolt insertion holes include a first lower fixing bolt insertion hole and a second lower fixing bolt insertion hole, which is disposed below the first lower fixing bolt insertion hole.

3. The glass strength evaluation apparatus of claim 2, wherein the first and second lower fixing bolt insertion holes are arranged along the vertical direction.

4. The glass strength evaluation apparatus of claim 1, wherein
the lower fixing bolt insertion holes include screw grooves on inner sidewalls thereof, and
the lower fixing bolts include screw threads corresponding to the screw grooves.

5. The glass strength evaluation apparatus of claim 1, further comprising:
a coupling unit connected to a lower part of the power unit,
wherein the fixing jig further includes a coupling head, which is connected to an upper part of the body portion and has a smaller outer diameter than an outer diameter of the body portion, and
the coupling unit further includes a head receiving portion, which receives the coupling head.

6. The glass strength evaluation apparatus of claim 5, wherein
a head fixing pin insertion hole penetrates the coupling head in a second horizontal direction intersecting the vertical direction from a first side of the coupling head to a second side of the coupling head, and
a first upper fixing pin insertion hole penetrates the coupling unit in the second horizontal direction from a first side of the coupling unit corresponding to the first side of the coupling head toward the head receiving portion, and
a second upper fixing pin insertion hole penetrates the coupling unit in the second horizontal direction from a second side of the coupling unit corresponding to the second side of the coupling head toward the head receiving portion.

7. The glass strength evaluation apparatus of claim 6, further comprising:
an upper fixing pin extending across the first upper fixing pin insertion hole, the head fixing pin insertion hole, and the second upper fixing pin insertion hole.

8. The glass strength evaluation apparatus of claim 1, further comprising:
a press-fitting member inserted in the press-fitting member insertion opening.

9. The glass strength evaluation apparatus of claim 8, wherein the press-fitting member extends in the vertical direction, a first end of the press-fitting member is exposed at the bottom of the body portion, and
a second end of the press-fitting member is inserted in the press-fitting member insertion opening.

10. The glass strength evaluation apparatus of claim 9, wherein the press-fitting member includes an indenter, which is disposed at the first end and has a ball shape.

11. The glass strength evaluation apparatus of claim 10, wherein the indenter has a diameter of about 0.3 millimeter to about 1 millimeter.

12. The glass strength evaluation apparatus of claim 11, wherein the indenter includes a chromium alloy (100Cr6).

13. The glass strength evaluation apparatus of claim 1, further comprising:
a load setting circuit which sets a load for the glass article and a descending speed of the power unit; and
a controller which controls an operation of the power unit.

14. The glass strength evaluation apparatus of claim 13, further comprising:
a sensor unit which is disposed on the surface of the plate and senses a load applied to the glass article and a breakage of the glass article.

15. The glass strength evaluation apparatus of claim 1, wherein the glass article has a thickness of about 50 micrometers to about 100 micrometers.

16. A glass strength evaluation method for testing a glass article, the method comprising:
placing the glass article including first and second surfaces on a surface of a plate such that an entirety of the second surface of the glass article contacts the surface of the plate;
lifting down a press-fitting member, which extends in a vertical direction and includes an indenter having a ball shape at one end of the press-fitting member, in the vertical direction such that the indenter contacts the first surface of the glass article; and
increasing a load applied to the first surface of the glass article through the indenter by gradually lifting down the press-fitting member in the vertical direction and determining whether the glass article is broken,
wherein the press-fitting member is in contact with two or more fixing bolts arranged in the vertical direction.

17. The glass strength evaluation method of claim 16, wherein the indenter has a diameter of about 0.3 millimeter to about 1 millimeter.

18. The glass strength evaluation method of claim 17, wherein the indenter includes a chromium alloy (100Cr6).

19. A glass strength evaluation method for testing a glass article, the comprising:
coupling a first press-fitting member, which extends in a vertical direction and includes a first indenter having a ball shape at one end of the first press-fitting member, to a fixing jig;
placing the fixing jig on a plate such that the first press-fitting member faces a top of the plate;
placing a first glass article included in the glass article and including first and second surfaces on a surface of the plate such that an entirety of the second surface of the first glass article contacts the surface of the plate;
lifting down the fixing jig such that the first indenter contacts the first surface of the first glass article; and
increasing a load applied to the first surface of the first glass article through the first indenter by gradually lifting down the fixing jig in the vertical direction and determining whether the first glass article is broken.

20. The glass strength evaluation method of claim 19, further comprising:
after the determining whether the first glass article is broken:
retrieving the first glass article and separating the first press-fitting member from the fixing jig;
coupling a second press-fitting member, which extends in the vertical direction and includes a second indenter having a ball shape at one end of the second press-fitting member, to the fixing jig;
placing the fixing jig on the plate such that the second press-fitting member faces the top of the plate;
placing a second glass article included in the glass article and including first and second surfaces on the surface of the plate such that an entirety of the second surface of the second glass article contacts the surface of the plate;
lifting down the fixing jig such that the second indenter contacts the first surface of the second glass article; and
increasing a load applied to the first surface of the second glass article through the second indenter by gradually lifting down the fixing jig in the vertical direction and determining whether the second glass article is broken.

* * * * *